(12) United States Patent
Shemesh et al.

(10) Patent No.: US 7,655,781 B2
(45) Date of Patent: Feb. 2, 2010

(54) VARIANTS OF HUMAN GLYCOPROTEIN HORMONE ALPHA CHAIN: COMPOSITIONS AND USES THEREOF

(75) Inventors: Ronen Shemesh, Modi'in (IL); Jeanne Bernstein, Kfar Yona (IL); Dvir Dahary, Tel Aviv (IL); Gil Shalev, Karkur (IL); Gideon Baum, HaShachar (IL); Yoseph Shaaltiel, Moshav Beit Hillel (IL)

(73) Assignees: Compugen Ltd., Tel Aviv (IL); Protalix Ltd., Carmiel (IL)

( * ) Notice: Subject to any disclaimer, the term of this patent is extended or adjusted under 35 U.S.C. 154(b) by 460 days.

(21) Appl. No.: 11/429,553

(22) Filed: May 5, 2006

(65) Prior Publication Data

US 2007/0298463 A1    Dec. 27, 2007

Related U.S. Application Data

(63) Continuation of application No. PCT/IL2004/001017, filed on Nov. 7, 2004, and a continuation of application No. 10/984,379, filed on Nov. 8, 2004, now abandoned.

(60) Provisional application No. 60/517,378, filed on Nov. 6, 2003.

(51) Int. Cl.
  *C07H 21/04* (2006.01)
  *C12N 15/16* (2006.01)
  *C12P 21/02* (2006.01)
  *C12N 15/05* (2006.01)
  *A61K 38/24* (2006.01)

(52) U.S. Cl. ............. 536/23.5; 435/69.1; 435/70.1; 435/252.3; 435/419; 530/399

(58) Field of Classification Search ............ None
See application file for complete search history.

(56) References Cited

U.S. PATENT DOCUMENTS

| | | | | |
|---|---|---|---|---|
| 5,367,110 | A | 11/1994 | Galili et al. | 800/205 |
| 6,242,580 | B1 | 6/2001 | Boime et al. | 530/398 |
| 6,306,654 | B1 | 10/2001 | Boime et al. | 435/360 |
| 6,361,992 | B1 | 3/2002 | Szkudlinski et al. | 435/320.1 |
| 6,625,545 | B1 | 9/2003 | Amitai et al. | 702/19 |
| 6,812,339 | B1 * | 11/2004 | Venter et al. | 536/24.31 |
| 2002/0169292 | A1 | 11/2002 | Weintraub et al. | 530/397 |
| 2004/0101876 | A1 | 5/2004 | Mintz et al. | 435/6 |
| 2004/0142325 | A1 | 7/2004 | Mintz et al. | 435/6 |

FOREIGN PATENT DOCUMENTS

WO    WO 98/13469    2/1998

OTHER PUBLICATIONS

Strausberg et al., NIH-MGC http:://MGC.NCI.NIH.GOV, Apr. 10, 2004, accessed Aug. 8, 2008.*

Wu et al. "Structure of human chorionic gonadotropin at 2.6 A resolution from MAD analysis of the selenomethionyl protein". Structure, vol. 2, Issue 6, Jun. 1994, pp. 545-558.
Shupnik et al., "Molecular biology of thyrotropin". Endocr. Rev. vol. 10, 1989, pp. 459-475.
Baenziger JU 1994 "Glycosylation and glycoprotein hormone function." In: Lustbander JW Puett D, Ruddon RW (eds) Glycoprotein hormones. Springer-Verlag, New York, pp. 167-174.
Fiddes et al., "The Gene Encoding the Common Alpha Subunit of the four Human Glycoprotein Hormones". J. Mol. Appl. Gen. 1981; vol. 1 pp. 3-18.
Dirnhofer S. et al. "Free α subunit of human chorionic gonadotrophin: molecular basis of immunologically and biologically active domains". Journal of Endocrinology 1994, 140: pp. 145-154.
Zygmunt M. et al. "Characterization of human chorionic gonadotropin as a novel angiogenic factor".J Clin Endocrinol Metab. Nov. 2002;87(11): pp. 5290-5296.
Hellens P. et al., "pGreen: a versatile and flexible binary Ti vector for Agrobacterium-mediated plant transformation". Plant Mol Biol. Apr. 2000;42(6): pp. 819-832.
Torres K.C. "Tissue culture techniques for horticultural crops". p. 111-114; 169-173.
Wurtele et al., "A Simple Efficient method for the Agrobacterium-mediated transformation of carrot callus cells". 1989, Plant Sci. 61: pp. 253-262.
Nasrallah, June B. et al "The *S* Gene family: Genes with Diverse structures and functions". 1995, Methods Mol. Biol. 55: pp. 63-72.
Suh, B.S. et al. "Introduction of a gonadotropin receptor expression plasmid into immortalized granulosa cells leads to reconstitution of hormone-dependent steroidogenesis" . J Cell Biol. Oct. 1992;119(2):439-50.
Keren-Tal I. et al, "Establishment of steroidogenic granulosa cell lines expressing follicle stimulating hormone receptors". Mol Cell Endocrinol. Sep. 1993;95(1-2):R1-10.
Amsterdam et al., "Generation and Application of Ovarian Steroidogenic Cell Lines". 2004, In: The Ovary, Chapter 22, Elsevier press, pp. 389-409.
Gordon D. F. et al. "Organization and nucleotide sequence of the mouse alpha-subunit gene of the pituitary glycoprotein hormones". DNA (New York). 1998:7(10): pp. 679-690.
Claverie J-M et al. "Alu alert". Nature. Oct. 27, 1994;371: p. 752.
Freimuth R.R. et al. "Human sulfotransferases SULT1C1 and SULT1C2: cDNA characterization, gene cloning, and chomosomal localization". Genomics. Apr. 15, 2000;65(2): pp. 157-165.
Kawarabayasi Y. et al. "Complete genome sequence of an aerobic hyper-thermophilic crenarchaeon, *Aeropyrum pernix* K1". DNA Res. Apr. 30, 1999;6(2):83-101.
"Embryogenesis In Carrot Cell Suspension Cultures" Cell Culture, pp. 169-173.

* cited by examiner

*Primary Examiner*—Lorraine Spector
(74) *Attorney, Agent, or Firm*—Winston & Strawn LLP

(57) ABSTRACT

The present invention provides human glycoprotein hormone (hGPH) α-chain splice variants, including isolated nucleic acids encoding these variants and the encoded amino acid sequences, as well as antibodies, antisense oligonucleotides, expression vectors and host cells comprising these sequences. The present invention further discloses the use of these sequences in the diagnosis, prevention and treatment of symptoms, diseases and disorders related to glycoprotein hormones.

10 Claims, 7 Drawing Sheets

```
                         1                                                    50
hGPH α-chain wt    MDYYRKYAAI FLVTLSVFLH VLHSAPDVQD CPECTLQENP FFSQPGAPIL hGPH α-chain V#1   MDYYRKYAAI FLVTLSVFLH VLHSAPDVQE TGFHHVAQAA LKLLSSSNPP hGPH α-chain V#2   MDYYRKYAAI FLVTLSVFLH VLHSAPDVQD CPECTLQENP FFSQPGAPIL hGPH α-chain V#3   MDYYRKYAAI FLVTLSVFLH VLHSAPDVQE TGFHHVAQAA LKLLSSSNPP hGPH α-chain V#4   MDYYRKYAAI FLVTLSVFLH VLHSAPDVQE TGFHHVAQAA LKLLSSSNPP 60                                                   100
hGPH α-chain wt    QCMGCCFSRA YPTPLRSKKT MLVQKNVTSE STCCVAKSYN RVTVMGGFKV hGPH α-chain V#1   TKASQSARIT DCPECTLQEN PFFSQPGAPI LQCMGCCFSR AYPTPLRSKK hGPH α-chain V#2   QCMGCCFSRA YPTPLRSKKT MLVQKNVTSE STCCVAKSYN RVRTSRSPEA hGPH α-chain V#3   TKASQSARIT GVSYCAGLID SF hGPH α-chain V#4   TKASQSARIT GVSYCAGLID SF 101                                                  147
hGPH α-chain wt    VENHTACHCS TCYYHKS hGPH α-chain V#1   TMLVQKNVTS ESTCCVAKSY NRVTVMGGFK VENHTACHCS TCYYHKS
hGPH α-chain V#2   F
```

FIGURE 1

Coding exon 1
```
gcagttactg agaactcata agacgaagct aaaatccctc ttcggatcca cagtcaaccg
ccctgaacac atcctgcaaa aagcccagag aaag
```

Coding exon 2
```
gagcgccatg gattactaca gaaaatatgc agctatcttt ctggtcacat tgtcggtgtt
tctgcatgtt ctccattccg ctcctgatgt gcagg
```

Alternative exon 2A
```
agacagggtt tcaccatgtt gcccaggctg ctctcaaact cctgagctca agcaatccac
ccactaaggc ctcccaaagt gctaggatta cag
```

Coding exon 3
```
attgcccaaa tgcacgctac aggaaaaccc attcttctcc cagccgggtg ccccaatact
tcagtgcatg ggctgctgct tctctagagc atatcccact ccactaaggt ccaagaagac
gatgttggtc caaaagaacg tcacctcaga gtccacttgc tgtgtagcta aatcatataa
cagg
```

Coding exon 4
```
gtcacagtaa tgggggggttt caaagtggag aaccacacgg cgtgccactg cagtacttgt
tattatcaca aatcttaaat gttttaccaa gtgctgtctt gatgactgct gattttctgg
aatggaaaat taagttgttt agtgtttatg gctttgtgag ataaaactct ccttttcctt
accataccac tttgacacgc ttcaaggata tactgcagct ttactgcctt cctccttatc
ctacagtaca atcagcagtc tagttctttt catttggaat gaatacagca ttaagcttgt
tccactgcaa ataaagcctt ttaaatcatc
```

FIGURE 2A

```
Met Asp Tyr Tyr Arg Lys Tyr Ala Ala Ile Phe Leu Val Thr Leu Ser
1             5                   10                  15
Val Phe Leu His Val Leu His Ser Ala Pro Asp Val Gln Glu Thr Gly
              20                  25                  30
Phe His His Val Ala Gln Ala Ala Leu Lys Leu Leu Ser Ser Ser Asn
              35                  40                  45
Pro Pro Thr Lys Ala Ser Gln Ser Ala Arg Ile Thr Asp Cys Pro Glu
    50                  55                  60
Cys Thr Leu Gln Glu Asn Pro Phe Phe Ser Gln Pro Gly Ala Pro Ile
65                  70                  75                  80
Leu Gln Cys Met Gly Cys Cys Phe Ser Arg Ala Tyr Pro Thr Pro Leu
                85                  90                  95
Arg Ser Lys Lys Thr Met Leu Val Gln Lys Asn Val Thr Ser Glu Ser
        100                 105                 110
Thr Cys Cys Val Ala Lys Ser Tyr Asn Arg Val Thr Val Met Gly Gly
        115                 120                 125
Phe Lys Val Glu Asn His Thr Ala Cys His Cys Ser Thr Cys Tyr Tyr
    130                 135                 140
His Lys Ser
145
```

FIGURE 2B

Coding exon 1
```
gcagttactg agaactcata agacgaagct aaaatccctc ttcggatcca cagtcaaccg
ccctgaacac atcctgcaaa aagcccagag aaag gagcgc catggattac tacagaaaat
```

Coding exon 2
```
gagcgccatg gattactaca gaaaatatgc agctatcttt ctggtcacat tgtcggtgtt
tctgcatgtt ctccattccg ctcctgatgt gcagg
```

Coding exon 3
```
attgcccaga atgcacgcta caggaaaacc cattcttctc ccagccgggt gccccaatac
ttcagtgcat gggctgctgc ttctctagag catatcccac tccactaagg tccaagaaga
cgatgttggt ccaaaagaac gtcacctcag agtccacttg ctgtgtagct aaatcatata
acagggtaag aacctcaaga tccccagaag ctttctaaca gcccaatcag agaaatgttc
atagagccca cccatggaat taatgccaa aggtgtctaa tgacccagcc tctgtcgagc
atttgtacag gtggggaata catttctacc cattaattaa aagagtcaat tgtcttgtgg
gtatagactg gatttattca gaatgaggag aataggggta gaggtgacaa ggggcaggtt
gggagaaagt acagcttact tgtgctaaaa atatttccta aaaggagac tgtgcaaatg
tagtatgcat ctacttattt cagcagaatg caaacaattt tatgtaatat tcttcaattt
tgtctctatc tatctatcta tcatctaatc tataatatgt tttttttcc ttcccttta
ggtcacagta agggggggttt caaagtggag aaccacacgg cgtgccactg cagtacttgt
tattatcaca aatcttaaat gttttaccaa gtgctgtctt gatgactgct gattttctgg
aatggaaaat taagttgttt agtgtttatg gctttgtgag ataaaactct ccttttcctt
accataccac tttgacacgc ttcaaggata tactgcagct ttactgcctt cctccttatc
ctacagtaca atcagcagtc tagttctttt catttggaat gaatacagca ttaagcttgt
tccactgcaa ataaagcctt ttaaatcatc
```

FIGURE 3A

```
Met Asp Tyr Tyr Arg Lys Tyr Ala Ala Ile Phe Leu Val Thr Leu Ser
1             5                   10                  15
Val Phe Leu His Val Leu His Ser Ala Pro Asp Val Gln Asp Cys Pro
              20                  25                  30
Glu Cys Thr Leu Gln Glu Asn Pro Phe Phe Ser Gln Pro Gly Ala Pro
              35                  40                  45
Ile Leu Gln Cys Met Gly Cys Cys Phe Ser Arg Ala Tyr Pro Thr Pro
          50              55                  60
Leu Arg Ser Lys Lys Thr Met Leu Val Gln Lys Asn Val Thr Ser Glu
65                  70                  75                  80
Ser Thr Cys Cys Val Ala Lys Ser Tyr Asn Arg Val Arg Thr Ser Arg
                  85                  90                  95
Ser Pro Glu Ala Phe
              100
```

FIGURE 3B

Coding exon 1
```
gcagttactg agaactcata agacgaagct aaaatccctc ttcggatcca cagtcaaccg
ccctgaacac atcctgcaaa aagcccagag aaag gagcgc catggattac tacagaaaat
```

Coding exon 2
```
gagcgccatg gattactaca gaaaatatgc agctatcttt ctggtcacat tgtcggtgtt
tctgcatgtt ctccattccg ctcctgatgt gcagg
```

Alternative exon 2A (connected to exon 3)
```
agacagggtt tcaccatgtt gcccaggctg ctctcaaact cctgagctca agcaatccac
ccactaaggc ctcccaaagt gctaggatta caggcgtgag ctactgtgct ggcctcatag
attctttttg agtcttttt ggatatttta ctctgccttt ttttttccct gatagattgc
ccagaatgca cgctacagga aaacccattc ttctcccagc cgggtgcccc aatacttcag
tgcatgggct gctgcttctc tagagcatat cccactccac taaggtccaa gaagacgatg
ttggtccaaa agaacgtcac ctcagagtcc acttgctgtg tagctaaatc atataacagg
```

Coding exon 4
```
gtcacagtaa tgggggggttt caaagtggag aaccacacgg cgtgccactg cagtacttgt
tattatcaca aatcttaaat gttttaccaa gtgctgtctt gatgactgct gattttctgg
aatggaaaat taagttgttt agtgtttatg gctttgtgag ataaaactct ccttttcctt
accataccac tttgacacgc ttcaaggata tactgcagct ttactgcctt cctccttatc
ctacagtaca atcagcagtc tagttctttt catttggaat gaatacagca ttaagcttgt
tccactgcaa ataaagcctt ttaaatcatc
```

FIGURE 4

Coding exon 1
```
gcagttactg agaactcata agacgaagct aaaatccctc ttcggatcca cagtcaaccg
ccctgaacac atcctgcaaa aagcccagag aaag gagcgc catggattac tacagaaaat
```

Coding exon 2
```
gagcgccatg gattactaca gaaaatatgc agctatcttt ctggtcacat tgtcggtgtt
tctgcatgtt ctccattccg ctcctgatgt gcagg
```

Alternative exon 2A (connected to exon 3 and exon 4 retaining introns)
```
agacagggtt tcaccatgtt gcccaggctg ctctcaaact cctgagctca agcaatccac
ccactaaggc ctcccaaagt gctaggatta caggcgtgag ctactgtgct ggcctcatag
attcttttg agtcttttt ggatatttta ctctgccttt ttttttccct gatagattgc
ccagaatgca cgctacagga aaacccattc ttctcccagc cgggtgcccc aatacttcag
tgcatggct gctgcttctc tagagcatat cccactccac taaggtccaa gaagacgatg
ttggtccaaa agaacgtcac ctcagagtcc acttgctgtg tagctaaatc atataacagg
gtaagaacct caagatcccc agaagctttc taacagccca atcagagaaa tgttcataga
gcccacccat ggaatttaat gccaaggtg tctaatgacc cagcctctgt cgagcatttg
tacaggtggg gaatacattt ctacccatta attaaaagag tcaattgtct tgtgggtata
gactggattt attcagaatg aggagaatag gggtagaggt gacaaggggc aggttgggag
aaagtacagc ttacttgtgc taaaaatatt tcctaaaaag gagactgtgc aaatgtagta
tgcatctact tatttcagca gaatgcaaac aattttatgt aatattcttc aattttgtct
ctatctatct atctatcatc taatctataa tatgttttt tttccttccc ctttaggtca
cagtaatggg gggtttcaaa gtggagaacc acacggcgtg ccactgcagt acttgttatt
atcacaaatc ttaaatgttt taccaagtgc tgtcttgatg actgctgatt ttctggaatg
gaaaattaag ttgtttagtg tttatggctt tgtgagataa aactctcctt ttccttacca
taccactttg acacgcttca aggatatact gcagctttac tgccttcctc cttatcctac
agtacaatca gcagtctagt tcttttcatt tggaatgaat acagcattaa gcttgttcca
ctgcaaataa agccttttaa atcatc
```

FIGURE 5

```
Met Asp Tyr Tyr Arg Lys Tyr Ala Ala Ile Phe Leu Val Thr Leu Ser
1              5                   10                  15
Val Phe Leu His Val Leu His Ser Ala Pro Asp Val Gln Glu Thr Gly
            20                  25                  30
Phe His His Val Ala Gln Ala Ala Leu Lys Leu Leu Ser Ser Ser Asn
            35                  40                  45
Pro Pro Thr Lys Ala Ser Gln Ser Ala Arg Ile Thr Gly Val Ser Tyr
    50                  55                  60
Cys Ala Gly Leu Ile Asp Ser Phe
65                  70
```

FIGURE 6

```
gcagttactg agaactcata agacgaagct aaaatccctc ttcggatcca cagtcaaccg
ccctgaacac atcctgcaaa aagcccagag aaaggagcgc catggattac tacagaaaat
atgcagctat ctttctggtc acattgtcgg tgtttctgca tgttctccat tccgctcctg atgtgcagga ttgcccagaa tgcacgctac aggaaaaccc attcttctcc cagccgggtg
ccccaatact tcagtgcatg ggctgctgct tctctagagc atatcccact ccactaaggt
ccaagaagac gatgttggtc caaaagaacg tcacctcaga gtccacttgc tgtgtagcta
aatcatataa cagggtcaca gtaatggggg gtttcaaagt ggagaaccac acggcgtgcc
actgcagtac ttgttattat cacaaatctt aaatgtttta ccaagtgctg tcttgatgac
tgctgatttt ctggaatgga aaattaagtt gtttagtgtt tatggctttg tgagataaaa
ctctcctttt ccttaccata ccactttgac acgcttcaag gatatactgc agctttactg
ccttcctcct tatcctacag tacaatcagc agtctagttc ttttcatttg gaatgaatac
agcattaagc ttgttccact gcaaataaag cctttttaaat catc
```

FIGURE 7A

```
Met Asp Tyr Tyr Arg Lys Tyr Ala Ala Ile Phe Leu Val Thr Leu Ser
1           5                   10                  15
Val Phe Leu His Val Leu His Ser Ala Pro Asp Val Gln Asp Cys Pro
                20                  25                  30
Glu Cys Thr Leu Gln Glu Asn Pro Phe Phe Ser Gln Pro Gly Ala Pro
            35                  40                  45
Ile Leu Gln Cys Met Gly Cys Cys Phe Ser Arg Ala Tyr Pro Thr Pro
        50              55                  60
Leu Arg Ser Lys Lys Thr Met Leu Val Gln Lys Asn Val Thr Ser Glu
65                  70                  75                  80
Ser Thr Cys Cys Val Ala Lys Ser Tyr Asn Arg Val Thr Val Met Gly
                85                  90                  95
Gly Phe Lys Val Glu Asn His Thr Ala Cys His Cys Ser Thr Cys Tyr
            100                 105                 110
Tyr His Lys Ser
        115
```

FIGURE 7B

SEQUENCE LISTING

<160> NUMBER OF SEQ ID NOS: 24

<210> SEQ ID NO 1
<211> LENGTH: 797
<212> TYPE: DNA
<213> ORGANISM: Artificial sequence
<220> FEATURE:
<223> OTHER INFORMATION: GPH alpha chain splice variant

<400> SEQUENCE: 1

```
gcagttactg agaactcata agacgaagct aaaatccctc ttcggatcca cagtcaaccg      60
ccctgaacac atcctgcaaa aagcccagag aaaggagcgc catggattac tacagaaaat     120
atgcagctat ctttctggtc acattgtcgg tgtttctgca tgttctccat tccgctcctg     180
atgtgcagga gacagggttt caccatgttg cccaggctgc tctcaaactc ctgagctcaa     240
gcaatccacc cactaaggcc tcccaaagtg ctaggattac agattgccca gaatgcacgc     300
tacaggaaaa cccattcttc tcccagccgg gtgccccaat acttcagtgc atgggctgct     360
gcttctctag agcatatccc actccactaa ggtccaagaa gacgatgttg gtccaaaaga     420
acgtcacctc agagtccact tgctgtgtag ctaaatcata taacagggtc acagtaatgg     480
ggggtttcaa agtggagaac cacacggcgt gccactgcag tacttgttat tatcacaaat     540
cttaaatgtt ttaccaagtg ctgtcttgat gactgctgat tttctggaat ggaaaattaa     600
```

```
gttgtttagt gtttatggct ttgtgagata aaactctcct tttccttacc ataccacttt      660
gacacgcttc aaggatatac tgcagcttta ctgccttcct ccttatccta cagtacaatc      720
agcagtctag ttcttttcat ttggaatgaa tacagcatta agcttgttcc actgcaaata      780 aagccttta aatcatc                                                      797
```

<210> SEQ ID NO 2
<211> LENGTH: 147
<212> TYPE: PRT
<213> ORGANISM: Artificial sequence
<220> FEATURE:
<223> OTHER INFORMATION: GPH alpha chain splice variant

<400> SEQUENCE: 2

```
Met Asp Tyr Tyr Arg Lys Tyr Ala Ala Ile Phe Leu Val Thr Leu Ser
 1               5                  10                  15

Val Phe Leu His Val Leu His Ser Ala Pro Asp Val Gln Glu Thr Gly
             20                  25                  30

Phe His His Val Ala Gln Ala Ala Leu Lys Leu Leu Ser Ser Ser Asn
         35                  40                  45

Pro Pro Thr Lys Ala Ser Gln Ser Ala Arg Ile Thr Asp Cys Pro Glu
     50                  55                  60

Cys Thr Leu Gln Glu Asn Pro Phe Phe Ser Gln Pro Gly Ala Pro Ile
 65                  70                  75                  80

Leu Gln Cys Met Gly Cys Cys Phe Ser Arg Ala Tyr Pro Thr Pro Leu
                 85                  90                  95

Arg Ser Lys Lys Thr Met Leu Val Gln Lys Asn Val Thr Ser Glu Ser
            100                 105                 110

Thr Cys Cys Val Ala Lys Ser Tyr Asn Arg Val Thr Val Met Gly Gly
        115                 120                 125

Phe Lys Val Glu Asn His Thr Ala Cys His Cys Ser Thr Cys Tyr Tyr
    130                 135                 140

His Lys Ser
145
```

<210> SEQ ID NO 3
<211> LENGTH: 1120
<212> TYPE: DNA
<213> ORGANISM: Artificial sequence
<220> FEATURE:
<223> OTHER INFORMATION: GPH alpha chain splice variant

<400> SEQUENCE: 3

```
gcagttactg agaactcata agacgaagct aaaatccctc ttcggatcca cagtcaaccg       60
ccctgaacac atcctgcaaa agcccagag aaaggagcgc catggattac tacagaaaat      120
atgcagctat ctttctggtc acattgtcgg tgtttctgca tgttctccat tccgctcctg      180
atgtgcagga ttgcccagaa tgcacgctac aggaaaaccc attcttctcc cagccgggtg      240
ccccaatact tcagtgcatg ggctgctgct tctctagagc atatcccact ccactaaggt      300
ccaagaagac gatgttggtc caaaagaacg tcacctcaga gtccacttgc tgtgtagcta      360
aatcatataa cagggtaaga acctcaagat ccccagaagc tttctaacag cccaatcaga      420
gaaatgttca tagagcccac ccatggaatt taatgccaaa ggtgtctaat gacccagcct      480
ctgtcgagca tttgtacagg tggggaatac atttctaccc attaattaaa agagtcaatt      540
gtcttgtggg tatagactgg atttattcag aatgaggaga ataggggtag aggtgacaag      600
gggcaggttg ggagaaagta cagcttactt gtgctaaaaa tatttcctaa aaaggagact      660
```

```
gtgcaaatgt agtatgcatc tacttatttc agcagaatgc aaacaatttt atgtaatatt     720
cttcaatttt gtctctatct atctatctat catctaatct ataatatgtt ttttttttcct    780 tccccttttag gtcacagtaa tgggggtttt caaagtggag aaccacacgg cgtgccactg    840
cagtacttgt tattatcaca aatcttaaat gttttaccaa gtgctgtctt gatgactgct     900
gattttctgg aatggaaaat taagttgttt agtgtttatg ctttgtgag ataaaactct      960 ccttttcctt accataccac tttgacacgc ttcaaggata tactgcagct ttactgcctt    1020
cctccttatc ctacagtaca atcagcagtc tagttctttt catttggaat gaatacagca   1080
ttaagcttgt tccactgcaa ataaagcctt ttaaatcatc                         1120
```

```
<210> SEQ ID NO 4
<211> LENGTH: 101
<212> TYPE: PRT
<213> ORGANISM: Artificial sequence
<220> FEATURE:
<223> OTHER INFORMATION: GPH alpha chain splice variant

<400> SEQUENCE: 4

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
        50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Arg Thr Ser Arg
                85                  90                  95

Ser Pro Glu Ala Phe
            100
```

```
<210> SEQ ID NO 5
<211> LENGTH: 879
<212> TYPE: DNA
<213> ORGANISM: Artificial sequence
<220> FEATURE:
<223> OTHER INFORMATION: GPH alpha chain splice variant

<400> SEQUENCE: 5
gcagttactg agaactcata agacgaagct aaaatccctc ttcggatcca cagtcaaccg      60
ccctgaacac atcctgcaaa aagcccgagag aaaggagcgc catggattac acagaaaat    120 atgcagctat ctttctggtc acattgtcgg tgtttctgca tgttctccat tccgctcctg    180
atgtgcagga cagggttt caccatgttg cccaggctgc tctcaaactc ctgagctcaa      240
gcaatccacc cactaaggcc tcccaaagtg ctaggattac aggcgtgagc tactgtgctg    300
gcctcataga ttcttttttga gtcttttttg gatatttac tctgcctttt ttttcccctg    360
atagattgcc cagaatgcac gctacaggaa aacccattct tctcccagcc gggtgcccca   420
atacttcagt gcatgggctg ctgcttctct agagcatatc ccactccact aaggtccaag   480
aagacgatgt tggtccaaaa gaacgtcacc tcagagtcca cttgctgtgt agctaaatca    540
tataacaggg tcagtgtaat gggggtttc aaagtggaga accacacggc gtgccactgc    600
agtacttgtt attatcacaa atcttaaatg ttttaccaag tgctgtcttg atgactgctg    660
```

```
attttctgga atggaaaatt aagttgttta gtgtttatgg ctttgtgaga taaaactctc    720
cttttcctta ccataccact ttgacacgct tcaaggatat actgcagctt tactgccttc    780
ctccttatcc tacagtacaa tcagcagtct agttcttttc atttggaatg aatacagcat    840
taagcttgtt ccactgcaaa taaagccttt taaatcatc                           879

<210> SEQ ID NO 6
<211> LENGTH: 72
<212> TYPE: PRT
<213> ORGANISM: Artificial sequence
<220> FEATURE:
<223> OTHER INFORMATION: GPH alpha chain splice variant

<400> SEQUENCE: 6

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Glu Thr Gly
            20                  25                  30

Phe His His Val Ala Gln Ala Ala Leu Lys Leu Leu Ser Ser Ser Asn
        35                  40                  45

Pro Pro Thr Lys Ala Ser Gln Ser Ala Arg Ile Thr Gly Val Ser Tyr
    50                  55                  60

Cys Ala Gly Leu Ile Asp Ser Phe
65                  70

<210> SEQ ID NO 7
<211> LENGTH: 1295
<212> TYPE: DNA
<213> ORGANISM: Artificial sequence
<220> FEATURE:
<223> OTHER INFORMATION: GPH alpha chain splice variant

<400> SEQUENCE: 7
gcagttactg agaactcata agacgaagct aaaatccctc ttcggatcca cagtcaaccg     60
ccctgaacac atcctgcaaa aagcccagag aaaggagcgc catggattac tacagaaaat    120
atgcagctat ctttctggtc acattgtcgg tgtttctgca tgttctccat tccgctcctg    180
atgtgcagga cagggtttt caccatgttg cccaggctgc tctcaaactc ctgagctcaa    240
gcaatccacc cactaaggcc tcccaaagtg ctaggattac aggcgtgagc tactgtgctg    300
gcctcataga ttcttttga gtctttttg gatattttac tctgccttt tttttccctg     360 atagattgcc cagaatgcac gctacaggaa aacccattct tctcccagcc gggtgcccca    420
atacttcagt gcatgggctg ctgcttctct agagcatatc ccactccact aaggtccaag    480
aagacgatgt tggtccaaaa gaacgtcacc tcagagtcca cttgctgtgt agctaaatca    540
tataacaggg taagaacctc aagatcccca gaagctttct aacagcccaa tcagagaaat    600
gttcatagag cccacccatg gaatttaatg ccaaggtgt ctaatgaccc agcctctgtc    660
gagcatttgt acaggtgggg aatacatttc tacccattaa ttaaaagagt caattgtctt    720
gtgggtatag actggattta ttcagaatga ggagaatagg ggtagaggtg acaagggggca   780 ggttgggaga agtacagct tacttgtgct aaaaatattt cctaaaaagg agactgtgca    840
aatgtagtat gcatctactt atttcagcag aatgcaaaca ttttatgta atattcttca    900 attttgtctc tatctatcta tctatcatct aatctataat atgttttttt ttccttcccc    960
tttaggtcac agtaatgggg ggtttcaaag tggagaacca cacggcgtgc cactgcagta   1020
cttgttatta tcacaaatct taaatgtttt accaagtgct gtcttgatga ctgctgattt   1080
```

```
tctggaatgg aaaattaagt tgtttagtgt ttatggcttt gtgagataaa actctccttt      1140
tccttaccat accactttga cacgcttcaa ggatatactg cagctttact gccttcctcc      1200
ttatcctaca gtacaatcag cagtctagtt cttttcattt ggaatgaata cagcattaag      1260
cttgttccac tgcaaataaa gccttttaaa tcatc                                 1295
```

<210> SEQ ID NO 8
<211> LENGTH: 704
<212> TYPE: DNA
<213> ORGANISM: Homo sapiens

<400> SEQUENCE: 8

```
gcagttactg agaactcata agacgaagct aaaatccctc ttcggatcca cagtcaaccg        60
ccctgaacac atcctgcaaa aagcccagag aaaggagcgc catggattac tacagaaaat       120
atgcagctat ctttctggtc acattgtcgg tgtttctgca tgttctccat tccgctcctg       180
atgtgcagga ttgcccagaa tgcacgctac aggaaaaccc attcttctcc cagccgggtg       240
ccccaatact tcagtgcatg ggctgctgct tctctagagc atatcccact ccactaaggt       300
ccaagaagac gatgttggtc caaaagaacg tcacctcaga gtccacttgc tgtgtagcta       360
aatcatataa cagggtcaca gtaatggggg gttttcaaagt ggagaaccac acggcgtgcc      420
actgcagtac ttgttattat cacaaatctt aaatgtttta ccaagtgctg tcttgatgac       480
tgctgatttt ctggaatgga aaattaagtt gtttagtgtt tatggctttg tgagataaaa       540
ctctcctttt ccttaccata ccactttgac acgcttcaag gatatactgc agctttactg       600
ccttcctcct tatcctacag tacaatcagc agtctagttc ttttcatttg gaatgaatac       660
agcattaagc ttgttccact gcaaataaag ccttttaaat catc                        704
```

<210> SEQ ID NO 9
<211> LENGTH: 116
<212> TYPE: PRT
<213> ORGANISM: Homo sapiens

<400> SEQUENCE: 9

```
Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115
```

<210> SEQ ID NO 10
<211> LENGTH: 616
<212> TYPE: DNA
<213> ORGANISM: Homo sapiens

<400> SEQUENCE: 10

```
agttactgag aactcataag acgaagctaa aatccctctt cggatccaca gtcaaccgcc    60
ctgaacacat cctgcaaaaa gcccagagaa aggagcgcca tggattacta cagaaaatat   120
gcagctatct ttctggtcac attgtcggtg tttctgcatg ttctccattc cgctcctgat   180
gtgcaggaga cagggtttca ccatgttgcc caggctgctc tcaaactcct gagctcaagc   240
aatccaccca ctaaggcctc ccaaagtgct aggattacag attgcccaga atgcacgcta   300
caggaaaacc cattcttctc ccagccgggt gccccaatac ttcagtgcat gggctgctgc   360
ttctctagag catatcccac tccactaagg tccaagaaga cgatgttggt ccaaaagaac   420
gtcacctcag agtccacttg ctgtgtagct aaatcatata cagggtcac agtaatgggg    480
ggtttcaaag tggagaacca cacggtcgtg ccactgcagt acttgtgatt atcacaaatc   540
ttaaatgttt taccaagtgc tgtcttgatg actgctgatt ttctggaatg gaaaattaag   600
ttgtctagtg tctatg                                                   616
```

<210> SEQ ID NO 11
<211> LENGTH: 339
<212> TYPE: DNA
<213> ORGANISM: Homo sapiens
<220> FEATURE:
<221> NAME/KEY: misc_feature
<222> LOCATION: (168)..(168)
<223> OTHER INFORMATION: n = unkonwn nucleotide
<220> FEATURE:
<221> NAME/KEY: misc_feature
<222> LOCATION: (224)..(224)
<223> OTHER INFORMATION: n = unkonwn nucleotide
<220> FEATURE:
<221> NAME/KEY: misc_feature
<222> LOCATION: (227)..(227)
<223> OTHER INFORMATION: n = unkonwn nucleotide
<220> FEATURE:
<221> NAME/KEY: misc_feature
<222> LOCATION: (251)..(251)
<223> OTHER INFORMATION: n = unkonwn nucleotide

<400> SEQUENCE: 11

```
gaaactttaa aacagctcag taccaggcca gttataacca gagcttttct agtcagcctc    60
accaagtaga acaaacagag cttcagcaag aacagcttca aacagtggtt ggcacttacc   120
atggttcccc agaccagtcc catcaagtga ctggtaacca ccagcagnct cctcagcaga   180
acactggatt tccacgtagc aatcagccct attacaatag tcgnggngtg tctcgtggag   240
gctcccgtgg ngctagaggc ttgatgaatg gataccgggg ccctgccaat ggattcagag   300
gaggatatga tgggttaccg cccttcattc tctcctccc                           339
```

<210> SEQ ID NO 12
<211> LENGTH: 458
<212> TYPE: DNA
<213> ORGANISM: Homo sapiens

<400> SEQUENCE: 12

```
gtgggctgct gcttctctag agcatatccc actccactaa ggtccaagaa gacgatgttg    60
gtccaaaaga acgtcacctc agagtccact tgctgtgtag ctaaatcata taacagggta   120
agaacctcaa gatccccaga agcttttcta cagcccaatc agagaaatgt tcatagagcc   180
cacccatgga atttaatgcc aaaggtgtct aatgacccag catctgtcga gcatttgtac   240
aggtggggaa tacattttcta cccattaatt aaaagagtca attgtcttgt gggtatagac   300
tggatttatt cagaatgagg agaatagggg tagaggtgac aaggggcagg ttgggagaaa   360
```

```
gtacagctta cttgtgctaa atatttcct aaaarggaga ctgtccaatg tagtatgcat    420
ctacttattt cagcagattg caaacaattt tttgtaat                          458

<210> SEQ ID NO 13
<211> LENGTH: 897
<212> TYPE: DNA
<213> ORGANISM: Homo sapiens

<400> SEQUENCE: 13
ggagttactg agaactcata agacgaagct aaaatccctc ttcggatcca cagtcaaccg    60
ccctgaacac atcctgcaaa aagcccagag aaaggagcgc catggattac tacagaaaat   120
atgcagctat ctttctggtc acattgtcgg tgtttctgca tgttctccat tccgctcctg   180
atgtgcagga ttgcccagaa tgcacgctac aggaaaagcc attcttctcc cagccgggtg   240
ccccaatact tcagtgcatg gctgctgct tctctagagc atatcccact ccactaaggt    300
ccaagaagac gatgtcggtc caaaagaacc gtcacctcag agtccacttg ctgtgtagct   360
caaatcatat aacagggtaa gaaccctcaag atccccagaa gctttctaac agcccaatca   420
gagaaatgtt catagagccc acccatggca atttaatggc caaaggtgta ctaatgaccc   480
agactctgtc gagcattggt acaggtgggg aatacatttc tacccattaa ttaaaagagt   540
caatgtcttg tgggtataga ctggattatc agaatgagga aatagggggt agaggtgaca   600
aggggcaagg tggggagaaa gttccaggtt acttgtggct aaaaatattt cctataaagg   660
agactgtgca aatgtagcta tggcatctaa cttattgacg acgaatggaa cgaactttat   720
ggtagatatt ctttgaatgt tggtgtctaa tctaatatat ctatagatct aatttataac   780
atggtgatga ttgagtatac cattaagtgt acagaaatgg ggggttcaag tggggaagaa   840 aaggggggtga atgggagagt ggagagtagt agacatcata tgggtagaca agtggtg      897

<210> SEQ ID NO 14
<211> LENGTH: 896
<212> TYPE: DNA
<213> ORGANISM: Homo sapiens

<400> SEQUENCE: 14
gagttactga gaactcataa gacgaagcta aaatccctct tcggatccac agtcaaccgc    60
cctgaacaca tcctgcaaaa agcccagaga aaggagcgcc atggattact acagaaaata   120
tgcagctatc tttctggtca cattgtcggt gtttctgcat gttctccatt ccgctcctga   180
tgtgcaggat tgcccagaat gcacgctaca ggaaaaccca ttcttctccc agccgggtgc   240 ccaatactt cagtgcatgg ctgctgctt ctctagagca tatcccatcc actaaggtcc    300
aagaagacga tgttggtcca aaagaacgtc acctcagagt ccactttgct gtgtagctaa   360
atcatataac agggtaagaa cctcaagatc cccagaagct tttctaacag cccaatcaga   420
gaaatgttca tagagcccag ccatggaatt taatgccaaa ggtgtctaat gacccaggct   480
ctgtcgaaca ttttgtaccg gtggccgaat accatttcta cccattaatt acaagagtca   540
attgtcctcg tgggtataga ctgggatttc attccgcaat gcaggcagc acatacgggt    600 taaaggtttt gacagggggg ccaggggttgc gcagaaccgc ttccagctta ctttgttgcc   660
taaaacatat ttgccttaca aagcgcgcct tggtggcaca tgtcgtatgc attctaccttt   720 tatttccggc acaatggcca accaattttt actgttacat attcttcca atttgtgccc    780 aatcaatcca atcctatcac tcttattcta tacaatgcgt tctttatgcc ttccccttta   840
```

```
ggctcacggt acgtggggg tctccacgct gcgcagaacc acacagcgtt gtgcca          896
```

<210> SEQ ID NO 15
<211> LENGTH: 31
<212> TYPE: PRT
<213> ORGANISM: Homo sapiens

<400> SEQUENCE: 15

His Val Ala Gln Ala Ala Leu Lys Leu Leu Ser Ser Ser Asn Pro Pro
1               5                   10                  15

Thr Lys Ala Ser Gln Ser Ala Arg Ile Thr Gly Val Ser Tyr Cys
            20                  25                  30

<210> SEQ ID NO 16
<211> LENGTH: 22
<212> TYPE: DNA
<213> ORGANISM: Artificial sequence
<220> FEATURE:
<223> OTHER INFORMATION: PCR primer

<400> SEQUENCE: 16

```
aaagcccaga gaaaggagcg cc                                              22
```

<210> SEQ ID NO 17
<211> LENGTH: 27
<212> TYPE: DNA
<213> ORGANISM: Artificial sequence
<220> FEATURE:
<223> OTHER INFORMATION: PCR primer

<400> SEQUENCE: 17

```
actttgaaac ccccccattac tgtgacc                                         27
```

<210> SEQ ID NO 18
<211> LENGTH: 23
<212> TYPE: DNA
<213> ORGANISM: Artificial sequence
<220> FEATURE:
<223> OTHER INFORMATION: PCR primer

<400> SEQUENCE: 18

```
gacagggttt caccatgttg ccc                                             23
```

<210> SEQ ID NO 19
<211> LENGTH: 23
<212> TYPE: DNA
<213> ORGANISM: Artificial sequence
<220> FEATURE:
<223> OTHER INFORMATION: PCR primer

<400> SEQUENCE: 19

```
ccttagtggg tggattgctt gag                                             23
```

<210> SEQ ID NO 20
<211> LENGTH: 26
<212> TYPE: DNA
<213> ORGANISM: Artificial sequence
<220> FEATURE:
<223> OTHER INFORMATION: PCR primer

<400> SEQUENCE: 20

```
attctgaata aatccagtct ataccc                                          26
```

<210> SEQ ID NO 21
<211> LENGTH: 41

```
<212> TYPE: DNA
<213> ORGANISM: Artificial sequence
<220> FEATURE:
<223> OTHER INFORMATION: PCR primer

<400> SEQUENCE: 21
acgcgtcgac aaaaatggat tactacagaa aaatatgcag c                          41

<210> SEQ ID NO 22
<211> LENGTH: 40
<212> TYPE: DNA
<213> ORGANISM: Artificial sequence
<220> FEATURE:
<223> OTHER INFORMATION: PCR primer

<400> SEQUENCE: 22
cggaattcct attaagattt gtgataataa caagtactgc                            40

<210> SEQ ID NO 23
<211> LENGTH: 18
<212> TYPE: DNA
<213> ORGANISM: Artificial sequence
<220> FEATURE:
<223> OTHER INFORMATION: PCR primer

<400> SEQUENCE: 23
ctcagaagac cagagggc                                                    18

<210> SEQ ID NO 24
<211> LENGTH: 17
<212> TYPE: DNA
<213> ORGANISM: Artificial sequence
<220> FEATURE:
<223> OTHER INFORMATION: PCR primer

<400> SEQUENCE: 24
caaagcggcc atcgtgc                                                     17
```

VARIANTS OF HUMAN GLYCOPROTEIN HORMONE ALPHA CHAIN: COMPOSITIONS AND USES THEREOF

CROSS-REFERENCE TO RELATED APPLICATION

This application is a continuation of International application PCT/IL2004/001017 filed Nov. 7, 2004 as well as a continuation of U.S. application Ser. No. 10/984,379 also filed Nov. 8, 2004, both of which claim the benefit of U.S. provisional application 60/517,378 filed Nov. 6, 2003. The entire content of each application is expressly incorporated herein by reference thereto.

FIELD OF THE INVENTION

The present invention relates to nucleic acid and amino acid variant sequences of human glycoprotein hormone α-chain, to compositions comprising same, and uses thereof in the diagnosis, prevention and treatment of symptoms, diseases and disorders related to glycoprotein hormones.

BACKGROUND OF THE INVENTION

The glycoprotein hormones, particularly those that are synthesized and secreted by the anterior pituitary gland can play important roles in a variety of physiological functions, including, for example, metabolism, temperature regulation, growth and reproduction. This family of evolutionarily conserved hormones includes the follicle-stimulating hormone (FSH), luteinizing hormone (LH), thyroid stimulating hormone (TSH), and chorionic gonadotropin (CG). Structurally, the glycoprotein hormones are heterodimers comprised of a common α-subunit and a hormone-specific β-subunit.

The two subunits are non-covalently linked to form a heterodimer, and the formation of the heterodimer has been shown to be required for receptor binding. Within a particular species, the α-subunits are identical among the glycoprotein hormones while the β-subunits differ and determine the receptor binding specificity of the particular hormone.

Structure-function relationships among the human glycoprotein hormones have been substantially based on models of gonadotropins, particularly hCG. The crystal structure of partially deglycosylated hCG revealed structural features that are also relevant to the other glycoprotein hormones (Lapthorn et al., 1994, Nature 369:455-461; Wu et al., 1994, Structure 2:548-558). The common α-subunit contains an apoprotein core of 92 amino acids including 10 cysteine residues, which forms pairs by disulfide linkage. The proposed cysteine pairs are 7-31, 10-60, 28-82, 32-84, and 59-87. Bonds 28-82 and 32-84 form a ring structure penetrated by a bond bridging cysteine residues 10 and 60 to result in a core—the cystine knot—that forms three hairpin loops. Both the α-subunit and the hCG β-subunit have a similar overall topology. Each subunit has two β-hairpin loops (L1 and L3) on one side of the central cystine knot (formed by three disulfide bonds), and a long loop (L2) on the other side.

The α-subunit is encoded by a single gene which is located on chromosome 6 in humans, and is identical in its amino acid sequence within a given species (Fiddes and Goodman, 1981, J. Mol. Appl. Gen. 1:3-18). The hormone specific β-subunit genes differ in length, structural organization and chromosomal localization (Shupnik et al., 1989, Endocr. Rev. 10:459-475).

The carbohydrate moiety of the glycoprotein hormones constitutes 15-35% by weight of the hormone. The common α-subunit comprises two asparagine (N)-linked oligosaccharides, and the β-subunit has one asparagine glycosylation site in TSH and LH and two in CG and FSH. In addition, the CG β-subunit has a unique 32-residue carboxyl-terminal extension peptide (CTEP) with four serine (O)-linked glycosylation sites. (Baenziger, 1994, in: Lustbander et al. (Eds.) Glycoprotein Hormones: Structure, Function and Clinical Implications. Springer-Verlag, New York, pages 167-174).

Following secretion, the glycoprotein hormones travel in the blood stream to the target cells, which contain membrane bound receptors. The hormone binds to the corresponding receptor and stimulates the cell. Typically, such stimulation involves an increase in activity of a specific intracellular regulatory enzyme which in turn catalyzes a biochemical reaction essential to the response of the cell. For example, binding of hCG to the hCG receptor present upon the corpus luteum (an ovarian structure), stimulates the activity of the enzyme adenylate cyclase. This enzyme catalyzes the conversion of intracellular ATP to cyclic AMP (cAMP). cAMP stimulates the activity of other enzymes involved in the production of ovarian steroid hormones, especially progesterone. hCG-stimulated progesterone secretion is essential for the maintenance of pregnancy during the first trimester of gestation. The exact mechanism by which a dimeric glycoprotein hormone, such as hCG, stimulates post-receptor events, such as activation of adenylate cyclase activity, is unknown. By a variety of experimental manipulations, it has been shown however, that accurate glycosylation plays important role in this regard. Treatment of glycoprotein hormones such as LH, FSH, or hCG with hydrogen fluoride removes approximately 70% of the oligosaccharide side chains. The resultant partially deglycosylated molecules retain their receptor binding activity but are unable to stimulate any post-receptor events. Glycosylation is also important in determining the hormone plasma half-life.

Soluble proteins containing cystine knot domains such as the glycoproteins are known to bind G-protein coupled receptors; other cystine knot proteins; glycoprotein hormone superfamily members; and glycoprotein hormone receptors. Thus, these multifunctional glycoproteins modulate a number of functions, including modulation of glycoprotein hormones-related protein activity, regulation of cellular proliferation, regulation of cellular differentiation and regulation of reproductive function.

U.S. Application No. 20020169292 discloses compositions and methods based on mutant Cystine Knot Growth Factors (CKGFs) comprising amino acid substitutions relative to the previously known hormone/growth factor. Specifically the application discloses mutated thyroid stimulating hormone (TSH) and chorionic gonadotropin (CG), which possessed modified bioactivities, including superagonist activity.

U.S. Pat. No. 6,361,992 discloses modified human glycoprotein hormone comprising modified α-chain in which certain amino acids are substituted with basic amino acids, specifically modified human glycoprotein hormone having increased activity over a wild-type hormone.

U.S. Pat. No. 6,306,654 discloses recombinantly produced human FSH which offers the opportunity for control of glycosylation pattern both on the α and β portions of the heterodimer. These obtained mutants have utility as antagonists and in altering pharmacokinetic activity of these hormones.

U.S. Pat. No. 6,242,580 discloses single-chain forms of the glycoprotein hormones, which may either be glycosylated, partially glycosylated, or nonglycosylated, and the α- and β-chains that occur in the native glycoprotein hormones or variants of them may optionally be linked through a linker moiety. The resulting single-chain hormones either retain the activity of the unmodified heterodimeric form or are antagonists of this activity.

Agonist and antagonist of the glycoprotein hormone α-chain can be used for screening, diagnosis and treatment of glycoprotein hormone related conditions, diseases or disorders, and for targeting of drugs or other therapeutic entities to cells bearing glycoprotein hormone receptors.

SUMMARY OF THE INVENTION

The present invention relates to isolated polynucleotides encoding novel variants of human glycoprotein hormone-α chain (hGPH-α chain), including recombinant DNA constructs comprising these polynucleotides, vectors comprising the constructs, host cells transformed therewith, and antibodies that recognize one or more specific epitope present on such splice variants.

The present invention provides isolated polynucleotides encoding novel splice variants of the α-subunit of human glycoprotein hormone (hGPH) including insertion variants, alternative exon usage and translatable intronic sequences.

The present invention further provides vectors, including expression vectors containing the polynucleotides of the invention, cells engineered to contain the polynucleotides of the present invention, cells genetically engineered to express the polynucleotides of the present invention, and methods of using same for producing recombinant hGPH α-chain splice variants according to the present invention.

The present invention also provides synthetic peptides comprising the novel amino acid sequences disclosed herein. It is explicitly to be understood that the novel splice variants disclosed herein as hGPH α-chain, whether deduced from conserved genomic DNA sequences, deduced from cDNA sequences, or derived from other sources, may be produced by any suitable method involving recombinant technologies, synthetic peptide chemistry or any combination thereof.

The present invention further provides pharmaceutical compositions comprising the novel hGPH α-chain splice variants or polynucleotide encoding same. The present invention provides methods for the diagnosis and treatment of hGPH related conditions, diseases or disorders comprising administering to a subject in need thereof a pharmaceutical composition comprising as an active ingredient a novel hGPH α-chain or a polynucleotide encoding same. The present invention further provides a method for targeting a drug or other therapeutic entity to a cell bearing glycoprotein hormone receptors.

According to one aspect, the present invention provides isolated polynucleotides encoding novel splice variants of hGPH α-chain. The present invention provides two types of the novel hGPH α-chain splice variants: One type comprises polynucleotides encoding polypeptides that retain high homology to the α-chain amino acid sequence of a native glycoprotein hormone, and another type encoding polypeptides comprising a unique amino acid sequence having homology to an eukaryotic protein of unknown function (DUF846, Pfam database: http://www.sanger.ac.uk/Software/Pfam/).

According to one embodiment the present invention provides isolated polynucleotides comprising nucleic acid sequences encoding novel splice variants of hGPH α-chain obtained by differential exon usage and/or intron retention.

According to another embodiment, the present invention provides an isolated polynucleotide comprising a nucleic acid sequence encoding a polypeptide having at least one novel hGPH α-chain agonist or antagonist activity. As described herein above, the degree of hGPH α-chain glycosylation plays an important role in the function of the glycoprotein. According to some embodiments the present invention provides splice variants with a different number of glycosylation sites of that of known α-chains.

Glycoprotein hormones are active when in the dimeric form, and the α-subunit contributes to the GPH/GPH receptor binding. A novel agonist of a hGPH α-chain polypeptide may therefore be defined as a polypeptide having at least one function that is at least similar if not identical to hGPH alpha-chain function(s), optionally and preferably including at least one activity selected from enhancing the association between the α- and β-chains; promoting binding of the hormone to the receptor; or inducing specificity of an α-chain to a certain β-chain. As it is anticipated that at least some of the novel hGPH splice variants may act as antagonists rather than agonists, and therefore prevent the formation of the dimeric form and the activity of the glycoprotein hormone, it is to be understood that these variants will be useful to prevent or diminish any pathological response mediated by a native glycoprotein hormone.

According to specific embodiments, the present invention provides an isolated polynucleotide comprising a nucleic acid sequence set forth in any one of SEQ ID NO:1, 3, 5, 7 or fragments, variants and analogs thereof. The present invention further provides the complement sequence for a polynucleotide having a nucleic acid sequence set forth in any one of SEQ ID NO:1, 3, 5, 7 or fragments, variants and analogs thereof. The polynucleotides of the present invention also include a polynucleotide that hybridizes to the complement of the nucleic acid sequence set forth in any one of SEQ ID NO:1, 3, 5, 7 or fragments, variants and analogs thereof under stringent hybridization conditions.

According to another specific embodiments, the present invention provides an isolated polynucleotide comprising a nucleic acid sequence encoding an amino acid sequence set forth in any one of SEQ ID NO:2, 4 and 6 or fragments, variants and analogs thereof.

According to certain embodiments, the present invention provides polynucleotides encoding polypeptides having at least one hGPH α-chain activity comprising unique amino acid sequences resulting from alternative splicing.

Thus, according to one embodiment, the present invention provides an isolated polynucleotide comprising a nucleic acid sequence encoding a polypeptide having at least one hGPH α-chain activity, wherein the polypeptide comprises contiguous amino acids having at least 80%, preferably at least 90%, more preferably 95% or more homology to positions 31 to 60 of SEQ ID NO:2. According to another embodiment, the present invention provides an isolated polynucleotide comprising a nucleic acid sequence encoding a polypeptide having at least one hGPH α-chain activity, wherein the polypeptide comprises contiguous amino acids having at least 80%, preferably at least 90%, more preferably 95% or more homology to the sequence RTSRSPEAF (positions 93-101 of SEQ ID NO:4). According to yet another embodiment, the present invention provides an isolated polynucleotide comprising a nucleic acid sequence encoding a polypeptide having at least one hGPH α-chain activity, wherein the polypeptide having at least 80%, preferably at least 95%, more preferably 95% homology to the amino acid sequence set forth in positions 30-72 set forth in SEQ ID NO:6. The degree of homology may be determined using appropriate alignment software as is known in the art.

It is to be understood that the present invention encompasses all active fragments, variants and analogs of the sequences disclosed herein that retain the biological activity of the sequence from which they are derived.

The invention also provides an isolated polynucleotide sequence comprising a nucleic acid sequence which hybridizes under stringent conditions to the nucleic acid sequence encoding the amino acid sequence set forth in any one of SEQ ID NO:2, 4, 6 or fragments, variants and analogs thereof. The invention further provides an isolated polynucleotide comprising the complement of the nucleic acid sequence encoding the amino acid sequence set forth in any one of SEQ ID NO:2, 4, 6, or fragments, variants and analogs thereof.

According to another aspect, the present invention provides novel polypeptide variants of an hGPH α-chain.

According to one embodiment, the present invention provides polypeptides having hGPH α-chain novel agonist or antagonist activity, as well as fragments, analogs and derivatives thereof. According to some embodiments, the polypeptides comprise all, part or none of the native hGPH α-chain glycosylation sites. Changes in one or more glycosylation sites in an alpha chain variant according to the present invention may also optionally provide at least one new or altered epitope for an antibody to specifically recognize.

According to another embodiment, the present invention provides an hGPH α-chain splice variant having an amino acid sequence set forth in any one of SEQ ID NO:2, 4, 6 or fragments, analogs and derivatives thereof.

According to one embodiment, the present invention provides an hGPH α-chain splice variant having an amino acid sequence comprising contiguous amino acids having at least 80%, preferably at least 90%, more preferably 95% or more homology to positions 31 to 60 of SEQ ID NO:2. According to another embodiment, the present invention provides an hGPH α-chain splice variant comprising contiguous amino acids having at least 80%, preferably 90%, more preferably 95% or more homology to an amino acid sequence RTSRSPEAF (positions 93-101 of SEQ ID NO:4). According to a further embodiment, the present invention provides an hGPH α-chain splice variant comprising contiguous amino acids having an amino acid sequence which is at least 80%, preferably at least 90%, more preferably at least 95% or more homologous to positions 30-72 set forth in SEQ ID NO:6.

According to another embodiments, the present invention relates to bridges, tails, and/or insertions, and/or analogs, homologs and derivatives of such peptides. Such bridges, tails, heads and/or insertions are described in greater detail below. As used herein a "tail" refers to a peptide sequence at the end of an amino acid sequence that is unique to a splice variant according to the present invention. Therefore, a splice variant having such a tail may optionally be considered as a chimera, in that at least a first portion of the splice variant is typically highly homologous (often 100% identical) to a portion of the corresponding known protein, while at least a second portion of the variant comprises the tail.

As used herein an "insertion" refers to a peptide sequence within an amino acid sequence that is unique to a splice variant according to the present invention. Therefore, a splice variant having such an insertion may optionally be considered as a chimera, in that at least a first and a third portions of the splice variant are typically highly homologous (often 100% identical) to a portion of the corresponding known protein, while at least a third portion comprises an insertion.

As used herein "an edge portion" refers to a connection between two portions of a splice variant according to the present invention that were not joined in the WT or known protein. An edge may optionally arise due to a join between the above "known protein" portion of a variant and the tail, for example, and/or may occur if an internal portion of the WT sequence is no longer present, such that two portions of the sequence are now contiguous in the splice variant that were not contiguous in the known protein. A "bridge" may optionally be an edge portion as described above, but may also include a join between an insertion and a "known protein" portion of a variant, or a join between a tail and a "known protein" portion of a variant.

According to preferred embodiments, the present invention provides an hGPH α-chain variant comprising a first portion having an amino acid sequence being at least about 90% homologous, preferably at least about 95% homologous to positions 1-29 of the amino acid sequence of WT hGPH α-chain (SEQ ID NO:9, which is GenBank record gi: 4502787), which are also amino acids 1-29 set forth in SEQ ID NO:2; a second insertion portion, having an amino acid sequence being at least about 80%, preferably at least about 85%, more preferably at least about 90%, most preferably at least about 95% homologous to an amino acid sequence ETGFHHVAQAALKLLSSSNPPTKASQSARIT (positions 30-60 of SEQ ID NO:2); and a third portion, having an amino acid sequence being at least about 90% homologous, preferably at least about 95% homologous to positions 30-116 of the amino acid sequence of previously known hGPH α-chain (SEQ ID NO:9), which are also amino acids 61-147 set forth in SEQ ID NO:2; wherein the first, second and third portions are contiguous and in sequential order.

According to another preferred embodiments, the present invention provides an insertion portion of hGPH α-chain variant having an amino acid sequence set forth in SEQ ID NO:2, wherein the insertion comprises an amino acid sequence at least about 80%, preferably at least about 85%, more preferably at least about 90%, most preferably at least about 95% homologous to the amino acid sequence ETGFHHVAQAALKLLSSSNPPTKASQSARIT. This peptide is present at positions 30-60 of the hGPH α-chain variant having an amino acid sequence set forth in SEQ ID NO:2.

According to another aspect, the novel splice variants as disclosed in the present invention comprise unique sequences in the regions joining or bridging the novel tail or insertion sequences to at least a portion of the previously known sequence of hGPH α-chain as set forth in SEQ ID NO:9. The unique joining or bridging region is a feature that characterizes the novel splice variants according to the present invention and distinguishes them from the previously known variants. This bridge portion may also comprise an epitope that is specific to the novel splice variants of the invention.

According to one preferred embodiment, the present invention provides a bridge portion of SEQ ID NO:2, comprising a peptide sequence having a length "n", wherein n is from about 4 to 50 amino acids, preferably from about 5 to 40 amino acids, more preferably 6-30 amino acids, the bridge portion comprising at least the dipeptide QE at positions 29-30 of SEQ ID NO:2, said bridge portion defined as follows (following the numbering set forth in SEQ ID NO:2): a sequence starting from any of amino acid numbers 29-x to 29; and ending at any of amino acid numbers 30+((n−2)−x), in which x varies from 0 to n−2; wherein the amino acid position number (as compared to SEQ ID NO:2) does not exceed 147.

According to another preferred embodiment, the present invention provides a bridge portion of SEQ ID NO:2, comprising a peptide sequence having a length "n", wherein n is from about 4 to 50 amino acids, preferably from about 5 to 40 amino acids, more preferably 6-30 amino acids, the bridge portion comprising at least the dipeptide TD at positions 60-61 of SEQ ID NO:2, said bridge portion defined as follows (following the numbering set forth in SEQ ID NO:2): a sequence starting from any of amino acid numbers 60-x to 60;

and ending at any of amino acid numbers 61+((n−2)−x), in which x varies from 0 to n−2; wherein the amino acid position number (as compared to SEQ ID NO:2) does not exceed 147.

According to yet another embodiment, the present invention provides an hGPH α-chain variant comprising a first portion having an amino acid sequence being at least about 90% homologous, preferably at least about 95% homologous to positions 1-92 of the amino acid sequence of WT (previously known) hGPH α-chain (SEQ ID NO:9), which are also positions 1-92 of SEQ ID NO:4; and a second (tail) portion, having an amino acid sequence being at least about 80%, preferably at least about 85%, more preferably at least about 90%, most preferably about 95% or more homologous to an amino acid sequence RTSRSPEAF (positions 93-101 of SEQ ID NO:4); wherein the first and the second portions are contiguous and in sequential order.

According to preferred embodiments, the present invention provides a tail portion of hGPH α-chain variant having an amino acid sequence set forth in SEQ ID NO:4, wherein the tail portion comprises an amino acid sequence at least about 80%, preferably at least about 85%, more preferably at least about 90%, most preferably at least about 95% or more homologous to an amino acid sequence RTSRSPEAF. This peptide is present at positions 93-101 of the hGPH α-chain variant having an amino acid sequence set forth in SEQ ID NO:4.

According to another preferred embodiment, the present invention provides a bridge portion of SEQ ID NO:4, comprising a peptide sequence having a length "n", wherein n is from about 4 to 50 amino acids, preferably from about 5 to 40 amino acids, more preferably 6-30 amino acids, the bridge portion comprising at least the dipeptide VR at positions 92-93 of SEQ ID NO:4, said bridge portion defined as follows (following the numbering set forth in SEQ ID NO:4): a sequence starting from any of amino acid numbers 92-x to 92; and ending at any of amino acid numbers 93+((n−2)−x), in which x varies from 0 to n−2; wherein the amino acid position number (as compared to SEQ ID NO:4) does not exceed 101.

According to further embodiments, the present invention provides an hGPH α-chain variant comprising a first portion having an amino acid sequence being at least about 90% homologous, preferably at least about 95% homologous to positions 1-29 of the amino acid sequence of WT (previously known) hGPH α-chain (SEQ ID NO:9), which are also positions 1-29 of SEQ ID NO:6; and a second (tail) portion, having an amino acid sequence being at least about 80%, preferably at least about 85%, more preferably about 90%, and most preferably about 95% homologous to an amino acid sequence ETGFHHVAQAALKLLSSSNPPT-KASQSARITGVSYCAGLIDSF (positions 30-72 of SEQ ID NO:6); wherein the first and the second portions are contiguous and in sequential order.

According to further preferred embodiments, the present invention provides a tail portion of hGPH α-chain variant having an amino acid sequence set forth in SEQ ID NO:6, wherein the tail portion comprises an amino acid sequence at least about 80%, preferably at least about 85%, more preferably about 90%, most preferably about 95% homologous to an amino acid sequence ETGFHHVAQAALKLLSSSNPPT-KASQSARITGVSYCAGLIDSF. This peptide is present at positions 30-72 of the hGPH α-chain variant having an amino acid sequence set forth in SEQ ID NO:6.

According to another preferred embodiment, the present invention provides a bridge portion of SEQ ID NO:6, comprising a peptide sequence having a length "n", wherein n is from about 4 to 50 amino acids, preferably from about 5 to 40 amino acids, more preferably 6-30 amino acids, the bridge portion comprising at least the dipeptide QE at positions 29-30 of SEQ ID NO:6, said bridge portion defined as follows (following the numbering set forth in SEQ ID NO:6): a sequence starting from any of amino acid numbers 29-x to 29; and ending at any of amino acid numbers 30+((n−2)−x), in which x varies from 0 to n−2; wherein the amino acid position number (as compared to SEQ ID NO:6) does not exceed 72.

According to yet another aspect, the present invention provides an expression vector containing at least a fragment of any of the polynucleotide sequences having a nucleotide sequence set forth in any one of SEQ ID NO:1, 3, 5, and 7. In yet another embodiment, the expression vector comprising the polynucleotide sequence is contained within a host cell.

The present invention further provides a method for producing the polypeptides according to the present invention comprising:
 a) culturing a host cell containing an expression vector containing at least a fragment of the polynucleotide sequence encoding an hGPH α-chain splice variant under conditions suitable for the expression of the polypeptide; and
 b) recovering the polypeptide from the host cell culture.

According to another aspect the present invention provides a method for detecting a polynucleotide which encodes an hGPH α-chain in a biological sample comprising:
 a) hybridizing the complement of a nucleic acid sequence which encodes a polypeptide having an amino acid sequence set forth in any one of SEQ ID NOS: 2, 4, and 6 to nucleic acid material of a biological sample, thereby forming a hybridization complex; and
 b) detecting the hybridization complex, wherein the presence of the complex correlates with the presence of a polynucleotide encoding an hGPH α-chain in the biological sample.

According to one embodiment the nucleic acid material of the biological sample is amplified by the polymerase chain reaction prior to hybridization.

According to yet another aspect the present invention provides a pharmaceutical composition comprising a polypeptide having an amino acid sequence set forth in any one of SEQ ID NO:2, SEQ ID NO:4, SEQ ID NO:6, or fragments, variants and analogs thereof, further comprising a pharmaceutically acceptable diluent or carrier. According to yet further aspect the present invention provides a pharmaceutical composition comprising a polynucleotide encoding a polypeptide having an amino acid sequence set forth in any one of SEQ ID NO:2, SEQ ID NO:4, SEQ ID NO:6, or fragments, variants and analogs thereof, further comprising a pharmaceutically acceptable diluent or carrier.

According to further aspects the present invention provides a purified inhibitor or antagonist of the hGPH α-chain splice variant of the present invention. The inhibitor or antagonist may be selected from the group consisting of antisense polynucleotides, antibodies, peptides, peptidomimetics and small organic molecules. The inhibitor, preferably a specific antibody, has a number of applications, including identification, purification and detection of variant hGPH α-chains, specifically any antibody capable of recognizing an epitope present on the hGPH splice variant that is absent from the known counterparts hGPH α-chains.

According to one embodiment, the present invention provides a purified antibody which binds to at least one specific epitope of a polypeptide comprising the amino acid sequence set forth in any one of SEQ ID NO:2, 4, 6, or fragments, analogs and derivatives thereof, with the proviso that the epitope is absent on the known counterpart hGPH α-chains.

Further aspects of the present invention provide methods for diagnosing, preventing, treating or ameliorating an hGPH related condition, disease or disorder comprising administering to a subject in need thereof a pharmaceutical composition comprising as an active ingredient an hGPH α-chain splice variant, a nucleic acid sequence encoding same, or an antagonist thereof as disclosed hereinabove.

According to one embodiment, the present invention provides a method for diagnosing, preventing, treating or ameliorating an hGPH related condition, disease or disorder comprising administering to a subject in need thereof a pharmaceutical composition comprising as an active ingredient a polypeptide comprising an amino acid sequence set forth in any one of SEQ ID NO:2, SEQ ID NO:4, and SEQ ID NO:6.

According to another embodiment, the present invention provides a method for preventing, treating or ameliorating an hGPH related disease or disorder, comprising administering to a subject in need thereof a pharmaceutical composition comprising as an active ingredient a polynucleotide encoding a polypeptide comprising an amino acid sequence set forth in any one of SEQ ID NO:2, SEQ ID NO:4, SEQ ID NO:6 and fragments, analogs and variants thereof.

According to yet another embodiment, the present invention provides a method for preventing, treating or ameliorating an hGPH related disease or disorder, comprising administering to a subject in need thereof a pharmaceutical composition comprising as an active ingredient a polynucleotide comprising nucleic acid sequence set forth in any one of SEQ ID NO:1, SEQ ID NO:3, SEQ ID NO:5, SEQ ID NO:7 and fragments, analogs and variants thereof.

According to further aspect the present invention provides a method for diagnosing GPH related conditions, diseases or disorders, comprising detecting specific expression of a polynucleotide comprising nucleic acid sequence set forth in any one of SEQ ID NO:1, SEQ ID NO:3, SEQ ID NO:5, SEQ ID NO:7 and fragments, analogs and variants thereof.

According to one embodiment, the detection of the expression is performed with a nucleic acid amplification technology (NAT) based assay. According to another embodiment, the detection is performed with an immunoassay.

According to further aspect the present invention provides a method for diagnosing GPH related conditions, diseases or disorders, comprising detecting specific expression of a polypeptide comprising an amino acid sequence set forth in any one of SEQ ID NO:2, SEQ ID NO:4, and SEQ ID NO:6 and fragments, analogs and variants thereof.

According to further aspects the present invention provides methods of inhibiting the expression of the hGPH α-chain splice variant by targeting the expressed transcript of such splice variant using antisense hybridization, si-RNA inhibition and ribozyme targeting.

According to yet another aspect, the present invention provides a method for targeting a drug or other therapeutic entity to a cell bearing an hGPH receptor. The carboxy-terminus of the α-subunit of the glycoprotein hormones contributes to the binding of the heterodimer hormone to its receptor. The α-chain may be therefore utilized for targeting a specific compound to the GPH receptors. Prior to targeting, the drug or its equivalent may be conjugated to the hGPH α-chain splice variant of the present invention by various methods, as is known to a person skilled in the art.

According to yet another aspect the present invention relates to hGPH α-chain splice variants capable of targeting a therapeutic or a diagnostic agent to a cell bearing GPH receptors.

According to one embodiment, the present invention provides a conjugate of the hGPH α-chain splice variant of the present invention with a therapeutic or a diagnostic agent.

According to another embodiment, the present invention provides a method for targeting a therapeutic or diagnostic agents to a cell bearing a GPH receptor, comprising administering to a subject in need thereof a pharmaceutical composition comprising as an active ingredient an hGPH-α-chain of the present invention conjugated to the therapeutic or diagnostic agent.

According to one embodiment, the therapeutic or the diagnostic agent is selected from the group consisting of a cytotoxic compound, a cytostatic compound, an antisense compound, an anti-viral agent, a specific antibody, a biodegradable carrier an imaging agent and a detection agent.

The present invention is explained in greater detail in the description, figures and claims below.

BRIEF DESCRIPTION OF THE DRAWINGS

FIG. 1 shows a comparison of the amino acid sequence of WT (previously known) hGPH α-chain and the amino acid sequences of the hGPH α-chain variants of the present invention.

FIG. 2 describes hGPH α-chain splice variant 1, having the nucleic acid sequence set forth in SEQ ID NO:1 (FIG. 2A) and its deduced amino acid sequence (SEQ ID NO:2, FIG. 2B).

FIG. 3 describes hGPH α-chain splice variant 2, having the nucleic acid sequence set forth in SEQ ID NO:3 (FIG. 3A) and its deduced amino acid sequence (SEQ ID NO:5, FIG. 3B).

FIG. 4 describes hGPH α-chain splice variant 3, having the nucleic acid sequence set forth in SEQ ID NO:5; its deduced amino acid sequence (SEQ ID NO:6) is shown in FIG. 6.

FIG. 5 describes hGPH α-chain splice variant 4, having the nucleic acid sequence set forth in SEQ ID NO:7; its deduced amino acid sequence (SEQ ID NO:6) is shown in FIG. 6.

FIG. 6 describes the polypeptide encoded by hGPH α-chain splice variants 3 (SEQ ID NO:5) and 4 (SEQ ID NO:7), having the amino acid sequence set forth in SEQ ID NO:6.

FIG. 7 describes the WT (previously known) hGPH α-chain (Accession Number NM 000735, SEQ ID NO:8; FIG. 7A) and its deduced amino acid sequence (SEQ ID NO:9; FIG. 7B).

DETAILED DESCRIPTION OF THE PREFERRED EMBODIMENTS

Figure 8:
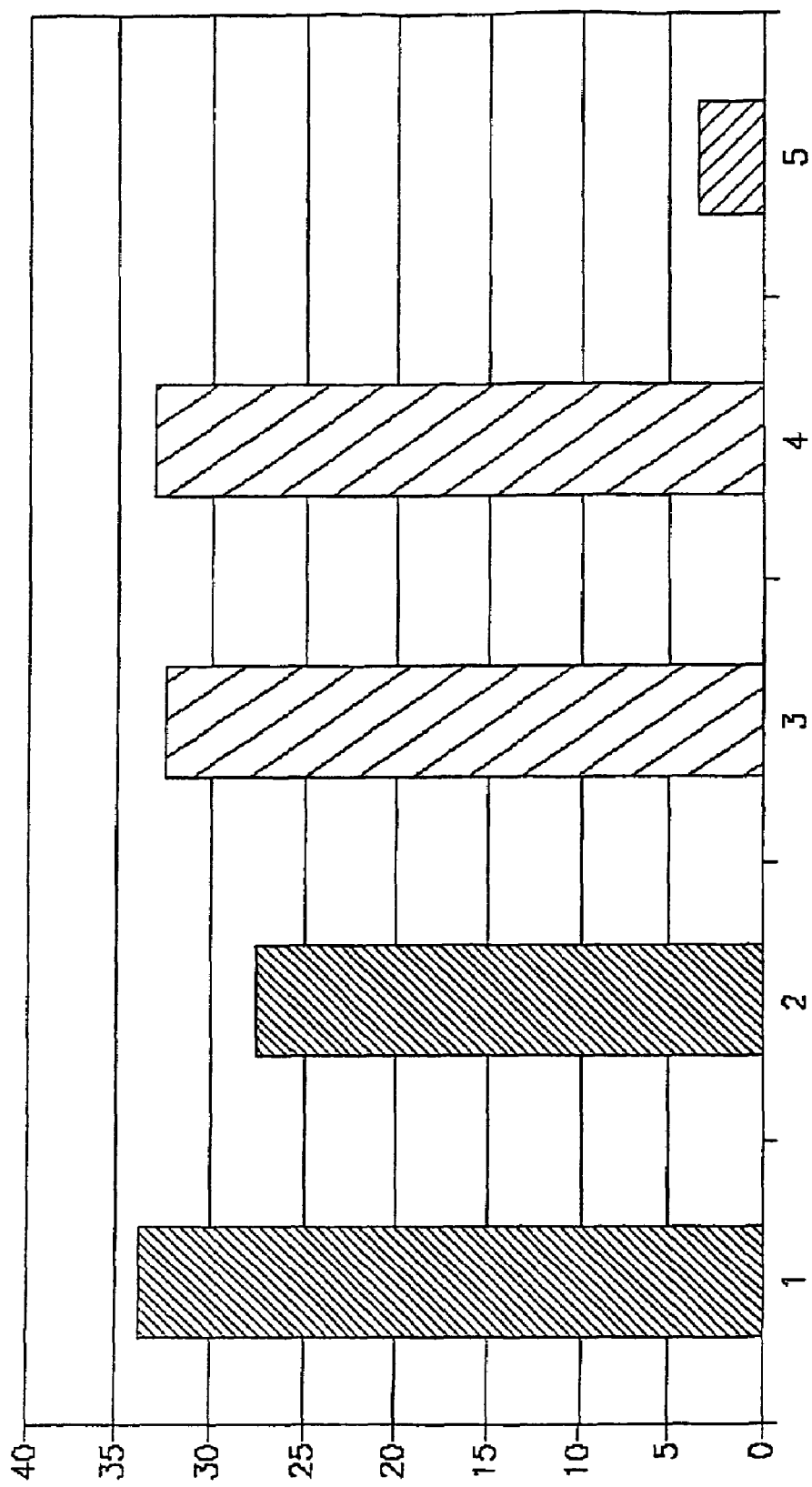
FIG. 8 shows FSH specific activity of a protein featuring either previously known (WT) or variant α-chain.

The present invention is directed to (i) novel splice variants of the known glycoprotein hormone α-chain (GPH α-chain); (ii) polynucleotide sequences encoding the novel splice variants; (iii) oligonucleotides and oligonucleotide analogs derived from said polynucleotide sequences; (v) antibodies recognizing said splice variants; (vi) peptides or peptide analogs derived from said splice variants; and (vii) pharmaceutical compositions; and (viii) methods of employing said polypeptides, peptides or peptide analogs; said oligonucleotides and oligonucleotide analogs; said polynucleotide sequences; and/or said antibodies, to regulate at least one GPH-α-chain mediated activity.

According to preferred embodiments, the present invention provides an hGPH α-chain variant comprising a first portion having an amino acid sequence being at least about 90% homologous, preferably at least about 95% homologous to positions 1-29 of the amino acid sequence of WT (previously known) hGPH α-chain (SEQ ID NO:9, which is GenBank record gi: 4502787), which are also positions 1-29 of SEQ ID NO:2; a second portion, having an amino acid sequence being at least about 80%, preferably at least about 85%, more preferably at least about 90%, most preferably at least about 95% homologous to an amino acid sequence ETGFHHVAQAALKLLSSSNPPTKASQSARIT (positions 30-60 of SEQ ID NO:2); and a third portion, having an amino acid sequence being at least about 90% homologous, preferably at least about 95% homologous to positions 30-116 of the amino acid sequence of WT hGPH α-chain (SEQ ID NO:9), which are also positions 61-147 of SEQ ID NO:2; wherein the first, second and third portions are contiguous and in sequential order.

According to another preferred embodiments, the present invention provides an insertion portion of hGPH α-chain variant having an amino acid sequence set forth in SEQ ID NO:2, wherein the insertion comprises an amino acid sequence at least about 80%, preferably at least about 85%, more preferably at least about 90%, most preferably at least about 95% homologous to the amino acid sequence ETGFHHVAQAALKLLSSSNPPTKASQSARIT. This peptide is present at positions 30-60 of the hGPH α-chain variant having an amino acid sequence set forth in SEQ ID NO:2.

According to yet another preferred embodiments, the present invention provides an hGPH α-chain variant comprising a first portion having an amino acid sequence being at least about 90% homologous, preferably at least about 95% homologous to positions 1-92 of the amino acid sequence of WT (previously known) hGPH α-chain (SEQ ID NO:9), which are also positions 1-92 of SEQ ID NO:4; and a second portion, having an amino acid sequence being at least about 90%, preferably at least about 95% homologous to an amino acid sequence RTSRSPEAF (positions 93-101 of SEQ ID NO:4); wherein the first and the second portions are contiguous and in sequential order.

According to yet further preferred embodiments, the present invention provides a tail portion of hGPH α-chain variant having an amino acid sequence set forth in SEQ ID NO:4, wherein the tail portion comprises an amino acid sequence at least about 80%, preferably at least about 85%, more preferably at least about 90%, most preferably at least about 95% or more homologous to an amino acid sequence RTSRSPEAF. This peptide is present at positions 93-101 of the hGPH α-chain variant having an amino acid sequence set forth in SEQ ID NO:4.

According to another preferred embodiments, the present invention provides an hGPH α-chain variant comprising a first portion having an amino acid sequence being at least about 90% homologous, preferably at least about 95% homologous to positions 1-29 of the amino acid sequence of WT hGPH α-chain (SEQ ID NO:9), which are also positions 1-29 of SEQ ID NO:6; and a second portion, having an amino acid sequence being at least about 80%, preferably at least about 85%, more preferably about 90%, most preferably about 95% homologous to an amino acid sequence ETGFHHVAQAALKLLSSSNPPTKASQSARITGVSYCAGLIDSF (positions 30-72 of SEQ ID NO:6); wherein the first and the second portions are contiguous and in sequential order.

According to further preferred embodiments, the present invention provides a tail portion of hGPH α-chain variant having an amino acid sequence set forth in SEQ ID NO:6, wherein the tail portion comprises an amino acid sequence at least about 80%, preferably at least about 85%, more preferably about 90%, most preferably about 95% homologous to an amino acid sequence ETGFHHVAQAALKLLSSSNPPTKASQSARITGVSYCAGLIDSF. This peptide is present at positions 30-72 of the hGPH α-chain variant having an amino acid sequence set forth in SEQ ID NO:6.

It should be noted that the hGPH α-chain variants according to the present invention clearly have different amino acid sequences and different nucleic acid sequences compared to the WT hGPH α-chain, as shown for example with regard to the amino acid sequences (FIG. 1; V#1=variant 1; V#2=variant 2; V#3=variant 3; V#4=variant 4). This comparison clearly emphasizes the differences between the splice variants of the present invention and the known protein. Moreover, it should be noted that the insertion of SEQ ID NO:2, the tail sequences of SEQ ID NO. 4, and the tail portion of SEQ ID NO:6 are unique sequences which are highly dissimilar to the sequence of WT hGPH α-chain.

According to another aspect, the novel splice variants as disclosed in the present invention comprise a unique sequence in the region joining or bridging the novel insertion or tail sequences to at least a portion of the previously known hGPH α-chain as set forth in SEQ ID NO:9. The unique joining or bridging region is a feature that characterizes the novel splice variants according to the present invention and additionally distinguishes them from the previously known alpha chain sequences. This bridge portion may also comprise an epitope that is specific to the novel splice variants of the invention.

According to one embodiment, the present invention provides a bridge portion of SEQ ID NO:2, comprising a peptide sequence having a length "n", wherein n is from about 4 to 50 amino acids, preferably from about 5 to 40 amino acids, more preferably 6-30 amino acids, the bridge portion comprising at least the dipeptide QE at positions 29-30 of SEQ ID NO:2, said bridge portion defined as follows (following the numbering set forth in SEQ ID NO:2): a sequence starting from any of amino acid numbers 29-x to 29; and ending at any of amino acid numbers 30+((n−2)−x), in which x varies from 0 to n−2; wherein the last amino acid position number (relative to SEQ ID NO:2) does not exceed 147.

According to another embodiment, the present invention provides a bridge portion of SEQ ID NO:2, comprising a peptide sequence having a length "n", wherein n is from about 4 to 50 amino acids, preferably from about 5 to 40 amino acids, more preferably 6-30 amino acids, the bridge portion comprising at least the dipeptide TD at positions 60-61 of SEQ ID NO:2, said bridge portion defined as follows (following the numbering set forth in SEQ ID NO:2): a sequence starting from any of amino acid numbers 60-x to 60; and ending at any of amino acid numbers 61+((n−2)−x), in which x varies from 0 to n−2; wherein the last amino acid position number (relative to SEQ ID NO:2) does not exceed 147.

According to yet another embodiment, the present invention provides a bridge portion of SEQ ID NO:4, comprising a peptide sequence having a length "n", wherein n is from about 4 to 50 amino acids, preferably from about 5 to 40 amino acids, more preferably 6-30 amino acids, the bridge portion comprising at least the dipeptide VR at positions 92-93 of SEQ ID NO:4, said bridge portion defined as follows (following the numbering set forth in SEQ ID NO:4): a sequence starting from any of amino acid numbers 92-x to 92; and ending at any of amino acid numbers 93+((n−2)−x), in which x varies from 0 to n−2; wherein the last amino acid position number (relative to SEQ ID NO:4) does not exceed 101.

According to further embodiment, the present invention provides a bridge portion of SEQ ID NO:6, comprising a peptide sequence having a length "n", wherein n is from about 4 to 50 amino acids, preferably from about 5 to 40 amino acids, more preferably 6-30 amino acids, the bridge portion comprising at least the dipeptide QE at positions 29-30 of SEQ ID NO:6, said bridge portion defined as follows (following the numbering set forth in SEQ ID NO:6): a sequence starting from any of amino acid numbers 29-x to 29; and ending at any of amino acid numbers 30+((n−2)−x), in which x varies from 0 to n−2; wherein the last amino acid position number (relative to SEQ ID NO:6) does not exceed 72.

For example, for bridge portion of SEQ ID NO:6 of 10 amino acids (such that n=10), the starting position could be as "early" in the sequence as amino acid number 21 if x=n−2=8 (i.e., 21=29−8), such that the peptide would end at amino acid number 30 (30+(8−8=0)). On the other hand, the peptide could start at amino acid number 29 if x=0 (i.e., 29=29−0), and could end at amino acid 38 (30+(8−0=8)).

According to other preferred embodiments, a bridge portion may optionally comprise a polypeptide being at least 80%, optionally at least about 85%, preferably at least about 90%, and more preferably at least about 95% homologous to at least one bridge sequence described above.

Similarly, the bridge portion may optionally be relatively short, such as from about 4 to about 9 amino acids in length. For example, a four amino acids bridge portion of SEQ ID NO:6 would comprise the following peptides: QETG; DVQE; VQET. All peptides feature QE as a portion thereof. Peptides of from about five to about nine amino acids could optionally be similarly constructed.

While conceiving the present invention it was hypothesized that additional, previously unknown, GPH α-chain variants may exist. Splice variants, which occur in over 50% of human genes, are usually overlooked in attempts to identify differentially expressed genes, as their unique sequence features including donor-acceptor concatenation, an alternative exon, an exon and a retained intron, complicate their identification. However, splice variants may have an important impact on the understanding of disease development and may serve as valuable markers in various pathologies.

Glycoprotein Hormone α-Chain Splice Variants

As used herein, "glycoprotein hormones" refers to the members of a family that includes follicle stimulating hormone (FSH), luteinizing hormone (LH), thyroid stimulating hormone (TSH) and chorionic gonadotropin (CG). All of these hormones are heterodimers comprised of α subunits which, for a given species, are identical in their amino acid sequence, and β subunits which differ according to the member of the family. Thus, normally these glycoprotein hormones occur as heterodimers composed of α and β subunits associated with each other but not covalently linked. Most vertebrates produce FSH, TSH and LH; chorionic gonadotropin has been found only in primates, including humans, and horses. The α-chain of all glycoprotein hormones comprises two unique glycosylation sites at asparagine residues. The splice variants of the present invention are characterized in that they retain at least one of the activities of the native GPH-α-chain, particularly human GPH α-chain. The splice variants of the present invention include splice variants which are the result of an insertion of a novel in-frame exon; splice variants resulted from the retention of native hGPH α-chain introns; and splice variants results from both—exon insertions and intron retentions.

The splice variants of the present invention differ in the number and location of glycosylation sites within the molecule. The variation in glycosylation sites can affect both the binding of the GPH-α-chain to GPH receptors, and the resulted signal transduction activity. The splice variants of the present invention also differ in their homology to the native hGPH α-chain domain. Thus, the splice variants of the present invention provide hGPH α-chain polypeptides which can serve as agonists or antagonists, for modulating lignad-receptor binding; receptor activation and signal trunsduction activity.

Before describing the present proteins, nucleotide sequences, the compositions comprising same and methods of use thereof, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells; reference to the "antibody" is a reference to one or more antibodies and equivalents thereof known to those skilled in the art; and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies, which are reported in the publications which might be used in connection with the invention. Nothing herein is to be construed as an admission that the invention is not entitled to antedate such disclosure by virtue of prior invention.

Definitions

GPH α-chain as used herein have in general its conventional definitions and refer to the proteins having the amino acid sequences of substantially purified GPH α-chain as in known in the art per se, or allelic variants thereof, regardless of the glycosylation pattern exhibited.

"Native" forms of these peptides are those which have the known amino acid sequences of peptides isolated from the relevant vertebrate tissue per se, or their allelic variants. The native forms are preferably purified from mammals, specifically human, and may be prepared from any source whether natural, synthetic, semi-synthetic, or recombinant.

As used herein, the phrase "genomic polynucleotide sequence" includes sequences which originally derive from a chromosome and reflect a contiguous portion of a chromosome.

The phrase "splice variants" refers to naturally occurring nucleic acid sequences and proteins encoded therefrom which are products of alternative splicing. Alternative splicing refers to intron inclusion, exon exclusion, 3' or 5' exon extension, alternative splice sites which leads to exon truncation, alternative exon usage or any addition or deletion of terminal sequences, which result in sequence dissimilarities between the splice variant sequence and other wild-type sequence(s). Although most alternatively spliced variants result from alternative exon usage, some result from the retention of introns not spliced-out in the intermediate stage of RNA transcript processing.

An "allele" or "allelic sequence", as used herein, is an alternative form of the gene encoding a GPH α-chain. Alleles may result from at least one mutation in the nucleic acid sequence and may result in altered mRNAs or polypeptides whose structure or function may or may not be altered. Any given natural or recombinant gene may have none, one, or many allelic forms. Common mutational changes, which give rise to alleles are generally ascribed to natural deletions, additions, or substitutions of nucleotides. Each of these types of changes may occur alone, or in combination with the others, one or more times in a given sequence.

"Altered" nucleic acid sequences encoding a GPH α-chain as used herein include those with deletions, insertions, or substitutions of different nucleotides resulting in a polynucleotide that encodes the same or a functionally equivalent GPH α-chain. Included within this definition are polymorphisms which may or may not be readily detectable using a particular oligonucleotide probe of the polynucleotide encoding a particular GPH α-chain, and improper or unexpected hybridization to alleles, with a locus other than the normal chromosomal locus for the polynucleotide sequence encoding the GPH α-chain. The encoded protein may also be "altered" and contain deletions, insertions, or substitutions of amino acid residues which produce a silent change and result in a functionally equivalent GPH α-chain. Deliberate amino acid substitutions may be made on the basis of similarity in polarity, charge, solubility, hydrophobicity, hydrophilicity, and/or the amphipathic nature of the residues as long as the biological or immunological activity of the GPH α-chain is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide or protein sequence, and fragment thereof, and to naturally occurring or synthetic molecules. Active fragments of GPH α-chain retain at least one biological activity or immunological activity or at least one antigenic epitope of the WT (previously known) GPH α-chain. Where "amino acid sequence" is recited herein to refer to an amino acid sequence of a protein molecule, amino acid sequence, and like terms, it is not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (for example, Dieffenbach and Dveksler 1995, PCR Primer, a Laboratory Manual, Cold Spring Harbor Press, Plainview, N.Y.).

The term "activatory ligand" or "agonist", as used herein, refers to a ligand that upon binding stimulates GPH signaling in a receptor-dependent manner. The term "inhibitory ligand" or "antagonist", as used herein, refers to a ligand which in the short term and/or longer term inhibits GPH signaling in a receptor-dependent manner. Without contradiction, under certain circumstances, a ligand may be correctly described either as activatory and inhibitory, depending on the environmental and experimental context in which it has been described.

The term "inhibitory ligand" or "antagonist", as used herein interchangeably, refers to a molecule which, when bound to a GPH receptor, decreases the amount or the duration of the effect of the biological or immunological activity of a known ligand of that receptor. Antagonists may include proteins, peptides, nucleic acids, antibodies or any other molecules which decrease the effect of a known GPH ligand.

As used herein, the term "antibody" refers to intact molecules as well as fragments thereof, which specifically binds and recognizes an epitope (e.g., an antigen). Preferably, the term refers to a polypeptide ligand substantially encoded by an immunoglobulin gene or immunoglobulin genes or fragments thereof, such as Fab, F(ab')2, Fv, scFv and the like, which are capable of binding the epitopic determinant. Antibodies that bind GPH ligand polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides are exemplified by bovine serum albumin, thyroglobulin and keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules also include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand. Antisense oligonucleotides are also used for modulation of alternative splicing in vivo and for diagnostics in vivo and in vitro (Khelifi C. et al., 2002, Current Pharmaceutical Design 8:451-1466; Sazani, P., and Kole. R. Progress in Molecular and Cellular Biology, 2003, 31:217-239).

The term "biologically active", as used herein, refers to a protein having structural, regulatory, or biochemical functions of a naturally occurring molecule. Likewise, "immunologically active" refers to the capability of the natural, recombinant, or synthetic GPH ligand, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of peptide nucleic acid (PNA) molecules.

As used herein, the phrase "complementary polynucleotide sequence" includes sequences which originally result from reverse transcription of messenger RNA using a reverse transcriptase or any other RNA dependent DNA polymerase. Such sequences can be subsequently amplified in vivo or in vitro using a DNA dependent DNA polymerase.

As used herein, the phrase "composite polynucleotide sequence" includes sequences which are at least partially complementary and at least partially genomic. A composite sequence can include some exonal sequences required to encode a polypeptide, as well as some intronic sequences interposed therebetween. The intronic sequences can be of any source, including of other genes, and typically will include conserved splicing signal sequences. Such intronic sequences may further include cis acting expression regulatory elements.

A "composition comprising a given polynucleotide sequence" as used herein refers broadly to any composition containing the given polynucleotide sequence. The composition may comprise a dry formulation or an aqueous solution. Compositions comprising polynucleotide sequences encoding a novel GPH α-chain splice variant according to the present invention (SEQ ID NO:2, 4 or 6), or fragments thereof may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to GPH α-chain or to the encoded GPH α-chain. Such modifications include, for example, replacement of hydrogen by an alkyl, acyl, or amino group. A nucleic acid derivative encodes a polypeptide that retains the biological or immunological function of the natural molecule. A derivative polypeptide is one that is modified by glycosylation, pegylation, or any similar process which retains at least one biological or immunological function of the polypeptide from which it was derived.

The phrase "differentially present" refers to differences in the quantity of a marker present in a sample taken from patients having the disease to be detected as compared to a comparable sample taken from healthy controls. For example, a nucleic acid fragment may optionally be differentially present between the two samples if the amount of the nucleic acid fragment in one sample is significantly different from the amount of the nucleic acid fragment in the other sample, for example as measured by hybridization and/or NAT-based assays. A polypeptide is differentially present between the two samples if the amount of the polypeptide in one sample is significantly different from the amount of the polypeptide in the other sample. It should be noted that if the marker is detectable in one sample and not detectable in the other, then such a marker could be considered to be differentially present.

As used herein the terms "diagnosing" or "diagnostic" refer to classifying a disease or a symptom, determining a severity of the disease, monitoring disease progression, forecasting an outcome of a disease and/or prospects of recovery. Diagnosis of a disease according to the present invention can be effected by determining a level of a polynucleotide or a polypeptide of the present invention in a biological sample obtained from the subject, wherein the level determined can be correlated with predisposition to, or presence or absence of the disease, or to its severity. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein, a "diagnostic amount" of a marker (a polynucleotide or a polypeptide of the present invention) refers to an amount of the marker in a subject's sample that is consistent with a diagnosis of hGPH α-chain related detectable disease. A diagnostic amount can be either in absolute amount (e.g., microgram/ml) or a relative amount (e.g., relative intensity of signals).

The term "homology", as used herein, refers to a degree of sequence similarity in terms of shared amino acid or nucleotide sequences. There may be partial homology or complete homology (i.e., identity). For amino acid sequence homology amino acid similarity matrices may be used as are known in different bioinformatics programs (e.g. BLAST, FASTA, Smith Waterman). Different results may be obtained when performing a particular search with a different matrix. Degrees of homology for nucleotide sequences are based upon identity matches with penalties made for gaps or insertions required to optimize the alignment, as is well known in the art (e.g. Altschul S. F. et al., 1990, J Mol Biol 215(3):403-10; Altschul S. F. et al., 1997, Nucleic Acids Res. 25:3389-3402).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

"Immunoassay" uses an antibody to specifically bind an antigen. The immunoassay is characterized by the use of specific binding properties of a particular antibody to isolate, target, and/or quantify the antigen. The phrase "specifically (or selectively) binds" to an antibody or "specifically (or selectively) immunoreactive with" when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample.

An "insertion" or "addition", as used herein, refers to a change in an amino acid or nucleotide sequence resulting in the addition of one or more amino acid residues or nucleotides, respectively, as compared to the naturally occurring molecule.

As used herein, the term "level" refers to expression levels of RNA and/or protein and/or anti-GPH α-chain splice variant antibody and/or antibody-antigen complexes or to DNA copy number of a marker of the present invention. The present invention preferably encompasses antibodies capable of selectively binding (with at least two fold higher binding) to at least one epitope of a GPH α-chain splice variant polypeptide according to the present invention as compared to any other polypeptide described herein, such as the previously described known WT GPH α-chain. The present invention also preferably encompasses any antibody-antigen complex formed with such antibodies and epitopes.

Typically the level of the marker in a biological sample obtained from a patient is different (i.e., increased or decreased) from the level of the same variant in a similar sample obtained from a healthy individual.

The term "marker" in the context of the present invention refers to a nucleic acid fragment, a peptide, or a polypeptide, which is differentially present in a sample taken from patients having a particular disease or condition as compared to a comparable sample taken from subjects who do not have the particular disease or condition. A "test amount" of a marker refers to an amount of a marker present in a sample being tested. A test amount can be either in absolute amount (e.g., microgram/ml) or a relative amount (e.g., relative intensity of signals). A "control amount" of a marker can be any amount or a range of amounts to be compared against a test amount of a marker. A control amount can be either in absolute amount (e.g., microgram/ml) or a relative amount (e.g., relative intensity of signals).

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of at least one GPH receptor mediated activity. For example, modulation may cause an increase or a decrease in protein activity, binding characteristics, or any other biological, functional or immunological properties of a GPH ligand.

"Nucleic acid sequence" as used herein refers to an oligonucleotide, nucleotide, or polynucleotide, and fragments thereof, and to DNA or RNA of genomic or synthetic origin, which may be single- or double-stranded, and represent the sense or antisense strand. "Fragments" are those nucleic acid sequences which are greater than 60 nucleotides in length, and most preferably include fragments that are at least 100 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

The term "peptide nucleic acid" (PNA) as used herein refers to nucleic acid "mimics"; the molecule's natural backbone is replaced by a pseudopeptide or peptide backbone and only the nucleotide base sequences are retained. The peptide backbone may end in lysine, which confers solubility to the composition. PNAs may be pegylated to extend their lifespan in the cell where they preferentially bind complementary single stranded DNA and RNA and stop transcript elongation.

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:10" encompasses the full-length native GPH α-chain and fragments thereof.

As used herein, a "primer" defines an oligonucleotide which is capable of annealing to a target sequence, thereby creating a double stranded region which can serve as an initiation point for DNA synthesis under suitable conditions.

The term "probe" refers to a GPH α-chain splice variant nucleic acid sequence according to the present invention, or a sequence complementary therewith, when used to detect presence of other similar sequences in a sample. The detection is carried out by identification of hybridization complexes between the probe and the assayed sequence. The probe may be attached to a solid support or to a detectable label.

The terms "sample" or "biological sample", as used herein, are used in their broadest sense. A biological sample suspected of containing nucleic acid encoding a GPH α-chain, or fragments thereof, or the encoded polypeptide itself may comprise a bodily fluid, extract from a cell, chromosome, organelle, or membrane isolated from a cell, a cell, genomic DNA, RNA, or cDNA in solution or bound to a solid support, a tissue, a tissue print, and the like. For example, a sample may include, but is not limited to, plasma, serum, spinal fluid, lymph fluid, the external sections of the skin, respiratory, intestinal, and genitourinary tracts, tears, saliva, milk, blood cells, tumors, neuronal tissue, organs, and also samples of in vivo cell culture constituents, amniotic fluid. Numerous well known tissue or fluid collection methods can be utilized to collect the biological sample from the subject in order to determine the level of DNA, RNA and/or polypeptide of the variant of interest in the subject. Examples include, but are not limited to, fine needle biopsy, needle biopsy, core needle biopsy and surgical biopsy (e.g., brain biopsy), as well as potentially less invasive methods such as lavage for example. Regardless of the procedure employed, once a biopsy is obtained the level of the variant can be determined and a diagnosis can thus be made. Determining the level of the same variant in normal tissues of the same origin is preferably effected along side to detect an elevated expression and/or amplification.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. to about 20-25° C. below the melting temperature of the probe). One or more factors be may be varied to generate conditions of either low or high stringency.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of GPH α-chain, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

Search for Novel GPH α-Chain Splice Variants

Utilizing a methodology of sequence comparison, it has been possible to identify hGPH α-chain splice variants utilizing a bioinformatics approach. The mRNA of the known human GPH α-chain (NM_000735, SEQ ID NO:8) was used for screening an EST database for novel splice variants using proprietary algorithm for clustering and assembly of nucleic acid sequences (the method for mRNA clustering and assembly used described in U.S. Pat. No. 6,625,545. The screening and annotation method described in U.S. Patent Application No. 20040101876 and 20040142325 assigned to the assignee of the present invention. Two splice variants were found based on ESTs: the first was based on EST 602592885F1, GenBank accession number BG571584 (SEQ ID NO:10), using human placenta NIH_MGC_79 library.

The second splice variant was based on the following ESTs: EST AV746586, GenBank accession number AV746586 (SEQ ID NO:11), using human pituitary NPC library; EST C17299, GenBank accession number C17299 (SEQ ID NO:12), using Clontech human aorta polyA+ mRNA (#6572), library; EST 602508788F1, GenBank accession number BG436344 (SEQ ID NO:13), using human placenta NIH_MGC_79 library; and EST 602508669F1, GenBank accession number BG436248 (SEQ ID NO:14), using human placenta NIH_MGC_79 library. These two EST-based novel splice variants (SEQ ID NOS:1, 3) comprise polynucleotides encoding polypeptides that retain high homology to the α-chain of a native glycoprotein hormone.

Additional two splice variants were obtained by a PCR reaction using primers designed for the amplification of the other two splice variants of the invention having SEQ ID NO:1 and NO:3.

Both variants were highly expressed in placenta, and to a lesser extent in the brain; one of the variants was also expressed in cervix and the other in the ovary, testis and prostate. These additional PCR-derived splice variants encode polypeptides comprising a unique amino acid sequence having homology to the eukaryotic protein of unknown function (DUF846, Pfam database) having the sequence HVAQAALKLLSSSNPPTKASQSARITGVSYC (SEQ ID NO:15).

Thus, according to one aspect the present invention provides isolated polynucleotides comprising a genomic, complementary or composite nucleic acid sequence encoding a novel splice variant of hGPH α-chain, wherein said splice variant is capable of binding and/or activating a GPH receptor.

According to one embodiment, the present invention provides an isolated polynucleotide comprising a nucleic acid sequence encoding a polypeptide having at least one novel hGPH α-chain agonist or antagonist activity.

According to some embodiments, the isolated polynucleotides of the present invention comprise a nucleic acid sequence of SEQ ID NOs:1, 3, 5, 7 or fragments, variants and analogs thereof. The present invention further provides the complement sequence for a polynucleotide having SEQ ID NO: 1, 3, 5, and 7 or fragments, variants and analogs thereof. The polynucleotide of the present invention also includes a polynucleotide that hybridizes to the complement of the nucleic acid sequence of SEQ ID NO: 1, 3, 5, and 7 under stringent hybridization conditions.

According to another embodiments, the isolated polynucleotide of the present invention encodes a polypeptide as set forth in SEQ ID NOS: 2, 4, 6, or a portion thereof, which retains at least one biological, immunological or other functional characteristic or activity of hGPH α-chain.

According to one embodiment, the present invention provides an isolated polynucleotide comprising a nucleic acid sequence encoding a polypeptide having an amino acid sequence set forth in any one of SEQ ID NO:2, 4 and 6.

It is to be understood that the present invention encompasses all active fragments, variants and analogs of the sequences disclosed herein that retain the biological activity of the sequence from which they are derived.

The invention also provides an isolated polynucleotide sequence which hybridizes under stringent conditions to the nucleic acid sequence encoding the amino acid sequence set forth in any one of SEQ ID NO:2, 4 and 6 or fragments of said polynucleotide sequences. The invention further provides an isolated polynucleotide sequence comprising the complement of the polynucleotide sequence encoding the amino acid sequence set forth in any one of SEQ ID NO:2, 4, 6, or fragments or variants of said polynucleotide sequence.

FIG. 2A shows the polynucleotide sequence of hGPH α-chain splice variant 1 (SEQ ID NO:1). FIG. 2B shows the deduced amino acid sequence of this variant (SEQ ID NO:2). FIG. 3A shows polynucleotide sequence of hGPH α-chain splice variant 2 (SEQ ID NO:3) and its deduced amino acid sequence (SEQ ID NO:4) is presented in FIG. 3A. FIGS. 4 and 5 show polynucleotide sequence of hGPH α-chain splice variant 3 (SEQ ID NO:5) and 4 (SEQ ID NO: 7), respectively, both encoding for the amino acid sequence set forth in FIG. 6 (SEQ ID NO:6).

Methods for DNA sequencing are well known and generally available in the art, and may be used to practice any of the embodiments of the invention. The methods may employ such enzymes as the Klenow fragment of DNA polymerase 1, Sequenase® (U.S. Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 377 DNA Sequencers (Perkin Elmer).

It will be appreciated by those skilled in the art that as a result of the degeneracy of the genetic code, a multitude of nucleotide sequences encoding the novel GPH-α-chain isoforms, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring hGPH α-chain variants, and all such variations are to be considered as being specifically disclosed.

According to one embodiment, the isolated polynucleotides of the present invention include a polynucleotide comprising a nucleotide sequence selected from the group consisting of SEQ ID NOs: 1, 3, 5 or 7.

Although nucleotide sequences which encode hGPH α-chain variants and their variants are preferably capable of hybridizing to the nucleotide sequence of the naturally occurring hGPH α-chain variants under appropriately selected conditions of stringency, it may be advantageous to produce nucleotide sequences encoding hGPH α-chain variants or their derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding hGPH α-chain variants and their derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode hGPH α-chain variants and their derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding hGPH α-chain variants or any fragment thereof.

The present invention also includes polynucleotide sequences that are capable of hybridizing to the nucleotide sequences according to the present invention. According to one embodiment, the polynucleotide is preferably hybridizable with SEQ ID NOS: 1, 3, 5, and 7.

Hybridization for long nucleic acids (e.g., above 200 bp in length) is effected according to preferred embodiments of the present invention by stringent or moderate hybridization. For example, stringent hybridization may be effected by hybridization at 65° C. with a hybridization solution containing 1% SDS, with a final wash solution of 0.2×SSC and 0.1% SDS at 65° C. Moderate hybridization may be effected by a hybridization solution containing 1% SDS at hybridization temperature of 65° C., with a final wash with a solution of 1×SSC and 0.1% SDS at 50° C.

According to preferred embodiments the polynucleotide according to this aspect of the present invention is as set forth in SEQ ID NO:1, or a portion thereof, said portion preferably encodes a polypeptide comprising contiguous amino acids having at least 80%, preferably at least 90%, more preferably 95% or more homology to positions 30 to 60 of SEQ ID NO:2. According to another preferred embodiments the polynucleotide according to this aspect of the present invention is as set forth in SEQ ID NO:3, or a portion thereof, said portion preferably encodes a polypeptide comprising contiguous amino acids having at least 80%, preferably at least 90%, more preferably 95% or more homology to a sequence RTSR-SPEAF, which is positions 93 to 101 of SEQ ID NO:4. According to yet another preferred embodiments the polynucleotide according to this aspect of the present invention is as set forth in SEQ ID NOs: 5, 7 or a portion thereof, said portion preferably encodes a polypeptide comprising contiguous amino acids having at least 80%, preferably at least 90%, more preferably 95% or more homology to positions 31-72 of SEQ ID NO:6.

According to still another embodiment of the present invention there is provided an oligonucleotide of at least 17, at least 18, at least 19, at least 20, at least 22, at least 25, at least 30 or at least 40, bases specifically hybridizable with the isolated nucleic acid described herein.

Hybridization of shorter nucleic acids (below 200 bp in length, e.g., 17-40 bp in length) is effected by stringent, moderate or mild hybridization. For example, stringent hybridization may be effected by a hybridization solution of 6×SSC and 1% SDS at hybridization temperature of 1-1.5° C. below the $T_m$, and final wash with solution of 3 M TMACl, 0.01 M sodium phosphate (pH 6.8), 0.5% SDS at 1-1.5° C. below the $T_m$. Moderate hybridization may be effected by a hybridization solution of 6×SSC, 0.1% SDS at hybridization temperature of 2-2.5° C. below the $T_m$, with final wash solution of 6×SSC at 22° C.; mild hybridization may be effected by a hybridization solution of 6×SSC and 1% SDS at 37° C., and final wash with solution of 6×SSC at 22° C.

According to an additional aspect the present invention provides a pair of oligonucleotides each independently of at least 17-40 bases specifically hybridizable with the isolated nucleic acid described herein in an opposite orientation so as to direct exponential amplification of a portion thereof, in a nucleic acid amplification reaction, such as a polymerase chain reaction (PCR). The polymerase chain reaction and other nucleic acid amplification reactions are well known in the art and require no further description herein. The pair of oligonucleotides according to this aspect of the present invention are preferably selected to have comparable melting temperatures ($T_m$), e.g., melting temperatures which differ by less than 7° C., preferably less than 5° C., more preferably less than 4° C., most preferably less than 3° C., typically between 3° C. and 0° C. Consequently, according to yet an additional aspect of the present invention there is provided a nucleic acid amplification product obtained using the pair of primers described herein. Such a nucleic acid amplification product can be isolated by gel electrophoresis or by any other size-based separation technique. Alternatively, such a nucleic acid amplification product can be isolated by affinity separation, either stranded affinity or sequence affinity. In addition, once isolated, such a product can be further genetically manipulated by restriction, ligation and the like, to serve any one of a plurality of applications associated with regulation of glycoprotein hormone activities as further detailed herein.

The nucleic acid sequences encoding hGPH α-chain may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar G., et al., 1993, PCR Methods Appl. 2:318-322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. The primers may be designed using commercially available software such as OLIGO 4.06 Primer Analysis software (National Biosciences Inc., Plymouth, Minn.), or another appropriate program, to be 22-30 nucleotides in length, to have a GC content of 50% or more, and to anneal to the target sequence at temperatures about 68° C. to 72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom M. et al., 1991, PCR Methods Appl. 1:111-119). In this method, multiple restriction enzyme digestions and ligations may also be used to place an engineered double-stranded sequence into an unknown fragment of the DNA molecule before performing PCR.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory region.

According to one embodiment, cDNA libraries are generated from specific tissue types, for EST sequencing. Basically, after a cDNA library from a tissue of interest is created, clones are randomly picked from these libraries and then single sequencing reactions from a large number of clones are performed. Each sequencing reaction generates about 300 base pairs of sequence that represents a unique sequence tag for a particular transcript.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In summary, this aspect of the present invention encompasses (i) polynucleotide sequences selected from the group consisting of SEQ ID NOS:1, 3, 5, or 7; (ii) fragments thereof; (iii) sequences hybridizable therewith; (iv) sequences homologous thereto; (v) sequences encoding similar polypeptides with different codon usage; (vi) altered sequences characterized by mutations, such as deletion, insertion or substitution of one or more nucleotides, either naturally occurring or man induced, either randomly or in a targeted fashion.

According to another aspect, the present invention provides novel polypeptide variants of hGPH α-chain.

According to one embodiment, the present invention provides polypeptides having hGPH α-chain agonist or antagonist activity, as well as fragments, analogs and variants thereof. According to some embodiments, the polypeptides comprise all, part or none of the native hGPH α-chain glycosylation sites. The glycosylation pattern of a particular protein may have considerable relevance to its biological activity. For example, it is well known in the case of human CG that desialylation cause the hormone to be cleared rapidly via the liver. It is also known that removal of carbohydrate internal to the sialic acid residues or complete deglycosylation converts human CG into an antagonist which binds more tightly to receptors but shows decreased biological activity. Other glycoproteins, such as, for example, tissue plasminogen activator, are also known to be altered in their degree of activity when the glycosylation pattern is changed. Thus, the glycosylation status of the hGPH α-chain splice variants of the present invention is particularly important for their mode of activity. The glycosylation status of a specific splice variant is mostly controlled by the presence of glycosylation sites within its amino acid sequence as well as by the expression system used, which may or may not allow the correct glycosylation to occur. A non-glycosylated variant may be produced utilizing a prokaryotic expression system. In a eukaryotic expression system the nature of the sugars occupying the glycosylation sites would be largely controlled by the nature of the specific host. Accordingly, a fine-tuning of the properties of the hormones of the invention can be achieved by proper choice of host. The therapeutic function of a particular glycoprotein hormone splice variant is also dependent on its glycosylation status.

According to one embodiment, the present invention provides an hGPH α-chain splice variant having the amino acid sequence set forth in any one of SEQ ID NO:2, 4, and 6. According to another embodiment, the present invention provides a hGPH α-chain splice variant having the amino acid sequence set forth in any one of SEQ ID NO: 2, 4, 6, or analogs, fragments and derivatives thereof, having at least one activity of the native hGPH α-chain.

According to one embodiment, the present invention provides an hGPH α-chain splice variant comprising contiguous amino acids having at least 80%, preferably at least 90%, more preferably 95% or more homology to positions 31 to 60 of SEQ ID NO:2. According to another embodiment, the present invention provides an hGPH α-chain splice variant having an amino acid sequence comprising contiguous amino acids having at least 80%, preferably at least 90%, more preferably 95% or more homology to a sequence RTSRS-PEAF (positions 93-101 of SEQ ID NO:4). According to a further embodiment, the present invention provides an hGPH α-chain splice variant having an amino acid sequence comprising contiguous amino acids which is at least 80%, preferably at least 90%, more preferably at least 95% or more homologous to amino acids 30-72 set forth in SEQ ID NO:6.

Producing the Novel Variants

Constructs Comprising the Novel Variants

According to another aspect the present invention provides a polynucleotide construct comprising the isolated nucleic acid described herein.

According to a preferred embodiment the nucleic acid construct according to this aspect of the present invention further comprises a promoter for regulating the expression of the isolated nucleic acid in a sense or antisense orientation. Such promoters are known to be cis-acting sequence elements required for transcription as they serve to bind DNA dependent RNA polymerase which transcribes sequences present downstream thereof. Such down stream sequences can be in either one of two possible orientations to result in the transcription of sense RNA which is translatable by the ribosome machinery or antisense RNA which typically does not contain translatable sequences, yet can duplex or triplex with endogenous sequences, either mRNA or chromosomal DNA and hamper gene expression, all as is further detailed hereinunder.

While the isolated nucleic acid described herein is an essential element of the invention, it is modular and can be used in different contexts. The promoter of choice that is used in conjunction with this invention is of secondary importance, and will comprise any suitable promoter sequence. It will be appreciated by one skilled in the art, however, that it is necessary to make sure that the transcription start site(s) will be located upstream of an open reading frame. In a preferred embodiment of the present invention, the promoter that is selected comprises an element that is active in the particular host cells of interest. These elements may be selected from transcriptional regulators that activate the transcription of genes essential for the survival of these cells in conditions of stress or starvation, including the heat shock proteins.

Vectors and Host Cells

In order to express a biologically active hGPH, the nucleotide sequences encoding hGPH α-chain or functional equivalents according to the present invention may be inserted into appropriate expression vector, i.e., a vector which contains the necessary elements for the transcription and translation of the inserted coding sequence.

Vectors can be introduced into cells or tissues by any one of a variety of known methods within the art, including in vitro recombinant DNA techniques, synthetic techniques, and in vivo genetic recombination. Such methods are generally described, for example, in Sambrook et al., Molecular Cloning: A Laboratory Manual, Cold Springs Harbor Laboratory, New York 1989, 1992; in Ausubel et al., Current Protocols in Molecular Biology, John Wiley and Sons, Baltimore, Md. 1989; Chang et al., Somatic Gene Therapy, CRC Press, Ann Arbor, Mich. 1995; Vega et al., Gene Targeting, CRC Press, Ann Arbor Mich. 1995; Vectors: A Survey of Molecular Cloning Vectors and Their Uses, Butterworths, Boston Mass. 1988; and include, for example, stable or transient transfection, lipofection, electroporation and infection with recombinant viral vectors. In addition, U.S. Pat. Nos. 5,464,764 and 5,487,992 disclose positive-negative selection methods.

A variety of expression vector/host systems may be utilized to contain and express sequences encoding hGPH α-chain. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed. The expression of the construct according to the present invention within the host cell may be transient or it may be stably integrated in the genome of the host cell.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript™ phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding hGPH α-chain splice variant, vectors based on SV40 or EBV may be used with an appropriate selectable marker.

In bacterial systems, a number of expression vectors may be selected depending upon the use intended for the hGPH α-chain. For example, when large quantities of hGPH α-chain are needed for the induction of antibodies, vectors which direct high-level expression of fusion proteins that are readily purified may be used. Such vectors include, but are not limited to, the multifunctional E. coli cloning and expression vectors such as Bluescript™ (Stratagene), in which the sequence encoding hGPH α-chain may be ligated into the vector in frame with sequences for the amino-terminal Met and the subsequent 7 residues of β-galactosidase so that a hybrid protein is produced; pIN vectors (Van Heeke G. and Schuster S. M. 1989, J Biol Chem 264:5503-5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH may be used. (Reviewed by, e.g., Ausubel et al. (supra)).

In cases where plant expression vectors are used, the expression of sequences encoding hGPH α-chain may be driven by any of a number of promoters. For example, viral promoters such as the 35S and 19S promoters of CaMV may be used alone or in combination with the omega leader sequence from TMV. Alternatively, plant promoters such as the small subunit of RUBISCO or heat shock promoters may be used. These constructs can be introduced into plant cells by direct DNA transformation or pathogen-mediated transfection. Such techniques are described in a number of generally available reviews (for example, Hobbs, S. or Murry, L. E. In: McGraw Hill Yearbook of Science and Technology (1992) McGraw Hill, New York, N.Y.; pp. 191-196).

An insect system may also be used to express an hGPH α-chain splice variant. For example, in one such system, *Autographa californica* nuclear polyhedrosis virus (AcNPV) is used as a vector to express foreign genes in *Spodoptera frugiperda* cells or in *Trichoplusia* larvae. The sequences encoding hGPH α-chain may be cloned into a non-essential region of the virus, such as the polyhedrin gene, and placed under control of the polyhedrin promoter. Successful insertion of hGPH α-chain will render the polyhedrin gene inactive and produce recombinant virus lacking coat protein. The recombinant viruses may then be used to infect, for example, *S. frugiperda* cells or *Trichoplusia* larvae in which hGPH α-chain may be expressed (Engelhard E. K. et al., 1994, Proc. Nat. Acad. Sci. 91:3224-3227).

In mammalian host cells, a number of viral-based expression systems may be utilized. In cases where an adenovirus is used as an expression vector, sequences encoding hGPH α-chain may be ligated into an adenovirus transcription/translation complex consisting of the late promoter and tripartite leader sequence. Insertion in a non-essential E1 or E3 region of the viral genome may be used to obtain a viable virus which is capable of expressing hGPH α-chain in infected host cells (Logan J. and Shenk T. 1984, Proc. Natl. Acad. Sci. 81:3655-3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than cannot be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding hGPH α-chain. Such signals include the ATG initiation codon and adjacent sequences. In cases where sequences encoding hGPH α-chain, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf K. D. et al., 1994, Results Probl. Cell Differ. 20:125-162).

Polypeptide Purification

The present invention further provides a method for producing the polypeptides according to the present invention comprising:
 a) culturing the host cell containing an expression vector containing at least a fragment of the polynucleotide sequence encoding a hGPH α-chain splice variant under conditions suitable for the expression of the polypeptide; and
 b) recovering the polypeptide from the host cell culture.

Host cells transformed with nucleotide sequences encoding hGPH α-chain splice variants according to the present invention may be cultured under conditions suitable for the expression and recovery of the protein from cell culture. The protein produced by a transformed cell may be secreted or contained intracellularly depending on the sequence and/or the vector used. According to the present invention, the polynucleotides encoding for an hGPH α-chain (SEQ ID NOS: 1, 3, 5 and 7) optionally and preferably include a signal peptide (amino acids at positions 1-25 of SEQ ID NOS: 2, 4 and 6) which direct secretion of the hGPH α-chain through a prokaryotic or eukaryotic cell membrane. Other constructions may be used to join sequences encoding hGPH α-chain to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences, such as those specific for Factor XA or enterokinase (Invitrogen, San Diego, Calif.), between the purification domain and the hGPH α-chain encoding sequence may be used to facilitate purification. One such expression vector provides for expression of a fusion protein containing hGPH α-chain and a nucleic acid encoding 6 histidine residues preceding a thioredoxin or an enterokinase cleavage site. The histidine residues facilitate purification on immobilized metal ion affinity chromatography. (IMIAC) (See, e.g., Porath J. et al., 1992, Prot. Exp. Purif. 3:263-281.) The enterokinase cleavage site provides a means for purifying hGPH α-chain from the fusion protein. (See, e.g., Kroll D. J. et al., 1993, DNA Cell Biol. 12:441-453.)

Fragments of hGPH α-chain may be produced not only by recombinant production, but also by direct peptide synthesis using solid-phase techniques. Protein synthesis may be performed by manual techniques or by automation. Automated synthesis may be achieved, for example, using the Applied Biosystems 431A peptide synthesizer (Perkin Elmer). Various fragments of hGPH α-chain splice variants may be synthesized separately and then combined to produce the full-length molecule.

Proteins

According to yet a further aspect of the present invention there is provided a recombinant or synthetic (i.e., prepared using solid phase peptide synthesis) protein comprising a polypeptide having at least one hGPH α-chain agonist or antagonist activity.

According to one certain embodiment the protein comprises an amino acid sequence set forth in any one of SEQ ID NO:2, 4 and 6 or fragments, derivatives and analogs thereof.

According to one embodiment, the hGPH α-chain variant comprises an amino acid sequence comprising contiguous amino acids having at least 80%, preferably at least 90%, more preferably 95% or more homology to positions 31 to 60 of SEQ ID NO:2. According to another embodiment, the variant comprise an amino acid sequence comprising contiguous amino acids having the sequence RTSRSPEAF (positions 93-101 of SEQ ID NO:4). According to a further embodiment, the hGPH α-chain variant comprises an amino acid sequence comprising contiguous amino acids having at least 80%, preferably at least 90%, more preferably at least 95% or more homology to amino acids 30-72 set forth in SEQ ID NO:6.

Additionally or alternatively, the polypeptide according to this aspect of the present invention is preferably encoded by a polynucleotide hybridizable with SEQ ID NOS: 1, 3, 5, or 7 or a portion thereof under any of stringent or moderate hybridization conditions. Still additionally or alternatively, the polypeptide according to this aspect of the present invention is preferably encoded by a polynucleotide sequence selected from the group consisting of SEQ ID NOS: 1, 3, 5, or 7 or portions thereof.

Thus, this aspect of the present invention encompasses (i) polypeptides as set forth in SEQ ID NOS: 2, 4, or 6; (ii) fragments thereof characterized by having at least one hGPH α-chain activity; (iii) polypeptides homologous thereto; and (iv) altered polypeptide characterized by mutations, such as deletion, insertion or substitution of one or more amino acids, either naturally occurring or man induced, either in random or in a targeted fashion, either natural, non-natural or modified at or after synthesis.

According to still a further aspect the present invention provides a pharmaceutical composition comprising as an active ingredient the recombinant protein according to the present invention as described herein, and a pharmaceutically acceptable diluent or carrier which is further described below.

Peptides

Peptides according to the present invention preferably comprise peptides according to the tail and/or insertion and bridge portions of the hGPH α-chain splice variants of the present invention, as described above.

As used herein the phrase "derived from a polypeptide" refers to peptides derived from the specified protein or proteins and further to homologous peptides derived from equivalent regions of proteins homologous to the specified proteins of the same or other species. The term further relates to permissible amino acid alterations and peptidomimetics designed based on the amino acid sequence of the specified proteins or their homologous proteins.

As used herein in the specification and in the claims section below the term "amino acid" is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid: hydroxylysine isodesmosine, nor-valine, nor-leucine and ornithine. Furthermore, the term "amino acid" includes both D- and L-amino acids. Further elaboration of the possible amino acids usable according to the present invention and examples of non-natural amino acids are given hereinunder.

Hydrophilic aliphatic natural amino acids can be substituted by synthetic amino acids, preferably Nleu, Nval and/or α-aminobutyric acid or by aliphatic amino acids of the general formula $HN(CH_2)_n COOH$, wherein n=3-5, as well as by branched derivatives thereof, wherein an alkyl group, for example, methyl, ethyl or propyl, is located at any one or more of the n carbons.

Each one, or more, of the amino acids can include a D-isomer thereof. Positively charged aliphatic carboxylic acids, such as, but not limited to, $H_2N(CH_2)_n COOH$, wherein n=2-4 and $H_2N—C(NH)—NH(CH_2)_n COOH$, wherein n=2-3, as well as by hydroxy Lysine, N-methyl Lysine or ornithine (Om) can also be employed. Additionally, enlarged aromatic residues, such as, but not limited to, $H_2N—(C_6H_6)—CH_2—COOH$, p-aminophenyl alanine, $H_2N—F(NH)—NH—(C_6H_6)—CH_2—COOH$, p-guanidinophenyl alanine or pyridinoalanine (Pal) can also be employed. Side chains of amino acid derivatives (if these are Ser, Tyr, Lys, Cys or Orn) can be protected-attached to alkyl, aryl, alkyloyl or aryloyl moieties. Cyclic derivatives of amino acids can also be used. Cyclization can be obtained through amide bond formation, e.g., by incorporating Glu, Asp, Lys, Om, di-amino butyric (Dab) acid or di-aminopropionic (Dap) acid at various positions is the chain (—CO—NH or —NH—CO bonds). Backbone to backbone cyclization can also be obtained through incorporation of modified amino acids of the formulas $H—N((CH_2)_n—COOH)—C(R)H—COOH$ or $H—N((CH_2)_n—COON)—C(R)H—NH_2$, wherein n=1-4, and further wherein R is any natural or non-natural side chain of an amino acid. Cyclization via formation of S—S bonds through incorporation of two Cys residues is also possible. Additional side-chain to side chain cyclization can be obtained via formation of an interaction bond of the formula $—(—CH_2—)_n—S—CH_2—C—$, wherein n=1 or 2, which is possible, for example, through incorporation of Cys or homoCys and reaction of its free SH group with, e.g., bromoacetylated Lys, Om, Dab or Dap. Peptide bonds (—CO—NH—) within the peptide may be substituted by N-methylated bonds (—N(CH₃)—CO—); ester bonds (—C(R)H—C—O—O—C(R)—N—); ketomethylen bonds (—CO—CH₂—); α-aza bonds (—NH—N(R)—CO—), wherein R is any alkyl, e.g., methyl; carba bonds (—CH₂—NH—); hydroxyethylene bonds (—CH(OH)—CH₂); thioamide bonds (—CS—NH—); olefinic double bonds (—CH=CH—); retro amide bonds (—NH—CO—); and peptide derivatives (—N(R)—CH₂—CO—), wherein R is the "normal" side chain, naturally presented on the carbon atom. These modifications can occur at any of the bonds along the peptide chain and even at several bonds (2-3) at the same time. Natural aromatic amino acids, Trp, Tyr and Phe, may be substituted for synthetic port-natural acid such as TIC, naphthylelanine (Nol), ring-methylated derivatives of Phe, halogenated derivatives of Phe or o-methyl Tyr.

Display Libraries

According to still another aspect of the present invention there is provided a display library comprising a plurality of display vehicles (such as phages, viruses or bacteria) each displaying at least 5-10 or 15-20 consecutive amino acids derived from a polypeptide selected from the group consisting of (a) a polypeptide comprising contiguous amino acids having at least 80%, more preferably at least 90%, more preferably 95% or more homology to positions 30 to 60 of SEQ ID NO:2; (b) a polypeptide comprising the sequence RTSRSPEAF (positions 93-101 of SEQ ID NO:4; and (c) a polypeptide comprising contiguous amino acids having at least 80%, more preferably at least 90%, more preferably 95% or more homology to positions 30 to 72 of SEQ ID NO:6.

According to a preferred embodiment of this aspect of the present invention substantially every 5-10 or 15-20 consecutive amino acids derived from a polypeptide described above are displayed by at least one at the plurality of display vehicles, so as to provide a highly representative library. Preferably, the consecutive amino acids or amino acid analogs of the peptide or peptide analog according to this aspect of the present invention are derived from any one of SEQ ID NO:2, 4, and 6, preferably from the contiguous amino acids at positions 31-60 of SEQ ID NO:2, positions 93-101 of SEQ ID NO:4 and positions 30-72 of SEQ ID NO:6.

Methods of constructing display libraries are well known in the art, such methods are described, for example, in Young A. C. et al., 1997, J Mol Biol 274:622-634; Giebel L. B. et al., 1995, Biochemistry 34(47):15430-15435; Davies E. L. et al., 1995, J Immunol Methods 186(1):125-35; Jones C. et al., 1995, J Chromatogr A 707(1):3-22; Deng S. J. et al., 1995, Proc Natl Acad Sci USA 92(11):4992-6; and Deng S. J. et al., 1994, J Biol Chem 269(13):9533-8, which are incorporated herein by reference.15435 Display libraries according to this aspect of the present invention can be used to identify and isolate polypeptides which are capable of up- or down-regulating GPH activity.

Antibodies

According to still another aspect the present invention provides antibodies useful for regulation of the expression of hGPH α-chain, affecting the GPH/GPH receptor interactions as described for antisense polynucleotides herein below. For example, it has been recently found (Dirnhofer S. et al., 1988. Prostate 35:212-220) that the gonadotropic glycoprotein hormones act directly on the prostatic gland, particularly FSH via FSH-receptor, thereby possibly modulating locally acting key hormones and growth factor involved in the development of benign prostate hyperplasia. Zygmunt M. et al., (2002, J. Clin. Endocrinol. Metabol. 87:5290-5296) demonstrated that hCG functions as an angiogenic factor, which may promotes uterine tumor invasion and metastasis. Thus, antagonizing the glycoprotein hormone-receptor interaction would have a therapeutically beneficial effect.

According to one embodiment, the present invention provides an antibody comprising an immunoglobulin specifically recognizing and binding a polypeptide having amino acid sequence set forth in any one of SEQ ID NO:2, 4 and 6.

According to a preferred embodiment of this aspect of the present invention the antibody specifically recognizes and binds to a polypeptide selected from the group consisting of (a) a polypeptide comprising contiguous amino acids having at least 80%, more preferably at least 90%, more preferably 95% or more homology to positions 30 to 60 of SEQ ID NO:2; (b) a polypeptide comprising the sequence RTSRSPEAF (positions 93-101 of SEQ ID NO:4; and (c) a polypeptide comprising contiguous amino acids having at least 80%, more preferably at least 90%, more preferably 95% or more homology to positions 30 to 72 of SEQ ID NO:6.

The present invention can utilize serum immunoglobulins, polyclonal antibodies or fragments thereof, (i.e., immunoreactive derivative of an antibody), or monoclonal antibodies or fragments thereof, either produced by the modification of whole antibodies or those synthesized de novo using recombinant DNA methodologies. Monoclonal antibodies of purified fragments of the monoclonal antibodies having at least a portion of an antigen bidding region, including such as Fab, F(ab')$_2$, Fv, scFv and the like (Harlow and Lane, 1988 Antibody, Cold Spring Harbor); single chain antibodies (U.S. Pat. No. 4,946,778); chimeric or humanized antibodies and complementarily determining regions (CDR) may be prepared by conventional procedures. These functional fragments of antibodies are described as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; and (6) complementarity-determining region (CDR) peptides ("minimal recognition units") which can be obtained by constructing genes encoding the CDR of an antibody of interest, for example, by using the polymerase chain reaction to synthesize the variable region from RNA of antibody-producing cells. (See, for example, Larrick and Fry 1991 Methods, 2:106-10).

Purification of these serum immunoglobulins antibodies or fragments can be accomplished by a variety of methods known to those skilled in the art including precipitation by ammonium sulfate or sodium sulfate followed by dialysis against saline, ion exchange chromatography, affinity or immunoaffinity chromatography as well as gel filtration, zone electrophoresis, etc. (Goding In: Monoclonal Antibodies: Principles and Practice, 2nd ed., pp. 104-126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes include IgD, IgE, IgA, IgM and related proteins.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow and Lane, 1988, Antibodies, A Laboratory Manual, for a description of immunoassay formats and conditions that can be used to determine specific immunoreactivity). Typically a specific or selective reaction will be at least twice the background signal or noise and more typically more than 10 to 100 times the background. For example, more preferably the antibodies bind specifically to epitope(s) of a hGPH α-chain splice variant of the present invention but do not bind to epitopes of known GPH proteins or variants (and/or bind at a much lower level, preferably being less than about half the level of binding to hGPH α-chain splice variant specific epitope(s)).

Monoclonal Antibodies

Methods for the generation and selection of monoclonal antibodies are well known in the art, as summarized for example in reviews such as Tramontano and Schloeder, 1989, Methods in Enzymology 178:551-568. A recombinant or synthetic hGPH α-chain splice variants or a portion thereof according to the present invention may be used to generate antibodies in vitro. More preferably, the recombinant or synthetic hGPH α-chain of the present invention is used to elicit antibodies in vivo. In general, a suitable host animal is immunized with the recombinant or synthetic hGPH α-chain of the present invention or a portion thereof including at least one continuous or discontinuous epitope. Advantageously, the animal host used is a mouse of an inbred strain. Animals are typically immunized with a mixture comprising a solution of the recombinant or synthetic hGPH α-chain of the present invention or portion thereof in a physiologically acceptable vehicle, and any suitable adjuvant, which achieves an enhanced immune response to the immunogen. By way of example, the primary immunization conveniently may be accomplished with a mixture of a solution of the recombinant or synthetic hGPH α-chain of the present invention or a portion thereof and Freund's complete adjuvant, said mixture being prepared in the form of a water-in-oil emulsion. Typically the immunization may be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding can be determined during the immunization schedule by any convenient method including by way of example radioimmunoassay, or enzyme linked immunosorbant assay, which is known as the ELISA assay. When suitable antibody titers are achieved, antibody-producing lymphocytes from the immunized animals are obtained, and these are cultured, selected and closed, as is known in the art. Typically, lymphocytes may be obtained in large numbers from the spleens of immunized animals, but they may also be retrieved from the circulation, the lymph nodes or other lymphoid organs. Lymphocyte are then fused with any suitable myeloma cell line, to yield hybridomas, as is well known in the art. Alternatively, lymphocytes may also be stimulated to grow in culture; and may be immortalized by methods known in the art including the exposure of these lymphocytes to a virus; a chemical or a nucleic acid such as an oncogene, according to established protocols. After fusion, the hybridomas are cultured under suitable culture conditions, for example in multiwell plates, and the culture supernatants are screened to identify cultures containing antibodies that recognize the epitope of choice. Hybridomas that secrete antibodies that recognize the recombinant or synthetic hGPH α-chain of the present invention are cloned by limiting dilution and expanded, under appropriate culture conditions. Monoclonal antibodies are purified and characterized in terms of immunoglobulin type and binding affinity.

Humanized Antibodies

Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., 1986, Nature, 321:522-525; Riechmann et al., 1988, Nature, 332:323-329; and Presta, 1992, Curr. Op. Struct. Biol., 2:593-596).

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (Jones et al., 1986, Nature, 321:522-525; Riechmann et al., 1988, Nature 332:323-327; Verhoeyen et al., 1988, Science, 239:1534-1536), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, 1991, J. Mol. Biol., 227:381; Marks et al., 1991, J. Mol. Biol., 222:581). The techniques of Cole et al. and Boemer et al. are also available for the preparation of human monoclonal antibodies (Cole et al., 1985, Monoclonal Antibodies and Cancer Therapy, Alan R. Liss, p. 77 and Boemer et al., 1991, J. Immunol., 147(1):86-95). Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., 1992, Bio/Technology 10:779-783; Lonberg et al., 1994, Nature 368:856-859; Morrison, 1994, Nature 368:812-13; Fishwild et al., 1996, Nature Biotechnology 14:845-51; Neuberger, 1996, Nature Biotechnology 14:826; and Lonberg and Huszar, 1995, Intern. Rev. Immunol. 13:65-93.

Use of the Novel Splice Variants

Further aspects of the present invention provide methods for diagnosing, preventing, treating or ameliorating an hGPH α-chain related condition, disease or disorder, comprising administering to a subject in need thereof a pharmaceutical composition comprising as an active ingredient an hGPH α-chain splice variant, or a nucleic acid sequence encoding same, as disclosed hereinabove.

Transgenic Animals or Cell Lines

The present invention has the potential to provide transgenic gene and polymorphic gene in animal and cellular (cell lines) models as well as for knockout and knock-in models. These models may be constructed using standard methods known in the art and as set forth in U.S. Pat. Nos. 5,487,992, 5,464,764, 5,387,742, 5,360,735, 5,347,075, 5,298,422, 5,288,846, 5,221,778, 5,175,385, 5,175,384, 5,175,383, 4,736,866 as well as Burke and Olson, 1991, Methods in Enzymology, 194:251-270; Capecchi, 1989, Science 244: 1288-1292; Davies et al., 1992, Nucleic Acids Research, 20(11):2693-2698; Dickinson et al., 1993, Human Molecular Genetics, 2(8):1299-1302; Huxley et al., 1991, Genomics, 9:7414 750 1991; Jakobovits et al., 1993, Nature, 362:255-261; Lamb et al., 1993, Nature Genetics, 5:22-29; Pearson and Choi, 1993, Proc. Natl. Acad. Sci. USA 90:10578-82; Rothstein, 1991, Methods in Enzymology, 194:281-301; Schedl et al., 1993, Nature, 362:258-261; Strauss et al., 1993, Science, 2591904-1907. Further, patent applications WO 94/23049, WO 93/14200, WO 94/06408, WO 94/28123 also provide information.

All such transgenic gene and polymorphic gene in animal and cellular (cell lines) models and knockout or knock-in models derived from claimed embodiments of the present invention, constitute preferred embodiments of the present invention.

Gene Therapy

Gene therapy as used herein refers to the transfer of genetic material (e.g., DNA or RNA) of interest into a host to treat or prevent a genetic or acquired disease or condition or phenotype. The genetic material of interest encodes a product (e.g., a protein, polypeptide, peptide, functional RNA, antisense) whose production in vivo is desired. For example, the genetic material of interest can encode a ligand, hormone, receptor, enzyme, polypeptide or peptide of therapeutic value. For review see, in general, the text "Gene Therapy" (Advanced in Pharmacology 40, 1997, Academic Press).

Two basic approaches to gene therapy have evolved: (i) ex vivo and (ii) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed, and then the modified cells are expanded in culture and returned to the host/patient. These genetically reimplanted cells have been shown to express the transfected genetic material in situ.

In in vivo gene therapy, target cells are not removed from the subject. Rather, the genetic material to be transferred is introduced into the cells of the recipient organism in situ, that is within the recipient. In an alternative embodiment, if the host gene is defective, the gene is repaired in situ. These genetically altered cells have been shown to express the transfected genetic material in situ. The gene expression vehicle is capable of delivery/transfer of heterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore, as used herein the expression vehicle may, as needed, not include the 5'UTR and/or 3'UTR of the actual gene to be transferred and only include the specific amino acid coding region.

The expression vehicle can include a promoter for controlling transcription of the heterologous material and can be either a constitutive or inducible promoter to allow selective transcription. Enhancers that may be required to obtain necessary transcription levels can optionally be included. Enhancers are generally any nontranslated DNA sequences which work contiguously with the coding sequence (in cis) to change the basal transcription level dictated by the promoter. The expression vehicle can also include a selection gene as described hereinbelow.

Vectors Useful in Gene Therapy

As described herein above, vectors can be introduced into host cells or tissues by any one of a variety of known methods within the art.

Introduction of nucleic acids by infection offers several advantages over the other listed methods; for example, higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector introducing and expressing recombination sequences is the adenovirus-derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Features that limit expression to particular cell type can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The natural specificity of viral vectors is utilized to specifically target predetermined cell types and thereby introduce a recombinant gene into the infected cell. The vector to be used in the methods of the invention will depend on the desired cell type to be targeted and will be known to those skilled in the art. For example, if breast cancer were to be treated then a vector specific for such epithelial cells would be used. Likewise, if diseases or pathological conditions of the hematopoietic system were to be treated, then a viral vector specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles, which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, they do not have to be administered locally at the diseased site. However, when local administration can provide a quicker and more effective treatment, administration can also be performed by, for example, intravenous or subcutaneous injection into the subject. Injection of the viral vectors into a spinal fluid can also be used as a mode of administration. Following injection, the viral vectors will circulate until they recognize cells with appropriate target specificity for infection.

Thus, according to an alternative embodiment, the nucleic acid construct according to the present invention further includes a positive and a negative selection markers and may therefore be employed for selecting for homologous recombination events, including, but not limited to, homologous recombination employed in knock-in and knockout procedures. One ordinarily skilled in the art can readily design a knockout or knock-in constructs including both positive and negative selection genes for efficiently selecting transfected embryonic stem cells that underwent a homologous recombination event with the construct.

Such cells can be introduced into developing embryos to generate chimeras, the offspring thereof can be tested for carrying the knockout or knock-in constructs. Knockout and/or knock-in constructs according to the present invention can be used to further investigate the functionality of hGPH α-chain, specifically the hGPH α-chain splice variants of the present invention. Such constructs can also be used in somatic and/or germ cells gene therapy to increase/decrease the activity of hGPH signaling, thus regulating hGPH related responses. Further detail relating to the construction and use of knockout and knock-in constructs can be found in Fukushige, S, and Ikeda, J. E., 1996, DNA Res 3:73-50; Bedell, M. A. et al., 1997, Genes and Development 11:1-11; Bermingham, J. J. et al., 1996, Genes Dev 10:1751-1762, which are incorporated herein by reference.

Antisense Polynucleotides

According to some embodiments the present invention provides antisense polynucleotides useful for regulation of the expression of hGPH α-chain, specifically the hGPH α-chain splice variants of the present invention, affecting the GPH/GPH receptor interactions. Diseases and disorders that are characterized by an increase (relative to a subject not suffering from the disease or disorder) in GPH levels or GPH-associated biological activity may be treated with therapeutics that antagonize, i.e., reduce or inhibit, activity. Therapeutics that antagonize activity may be administered in a therapeutic or prophylactic manner.

Thus, according to an additional embodiment of the present invention there is provided an antisense oligonucleotide comprising a polynucleotide or a polynucleotide analog of at least 10 bases, preferably between 10 and 15, more preferably between 5 and 20 bases, most preferably, at least 17-40 bases being hybridizable in vivo, under physiological conditions, with a portion of a polynucleotide strand encoding an hGPH α-chain splice variant having an amino acid sequence set forth in any one of SEQ ID NOS: 2, 4, and 6.

According to one preferred embodiment, the present invention provides an antisense oligonucleotide comprising a polynucleotide or a polynucleotide analog of at least 10 bases, preferably between 10 and 15, more preferably between 5 and 20 bases, most preferably, at least 17-40 bases being hybridizable in vivo, under physiological conditions, with a portion of a polynucleotide strand encoding a polypeptide selected from the group consisting of (a) a polypeptide comprising contiguous amino acids having at least 80%, more preferably at least 90%, more preferably 95% or more homology to positions 30 to 60 of SEQ ID NO:2; (b) a polypeptide comprising the sequence RTSRSPEAF (positions 93-101 of SEQ ID NO:4; and (c) a polypeptide comprising contiguous amino acids having at least 80%, more preferably at least 90%, more preferably 95% or more homology to positions 30 to 72 of SEQ ID NO:6.

According to one preferred embodiment, the present invention provides an antisense oligonucleotide comprising a polynucleotide or a polynucleotide analog of at least 10 bases, preferably between 10 and 15, more preferably between 5 and 20 bases, most preferably, at least 17-40 bases being hybridizable in vivo, under physiological conditions, with a portion of a polynucleotide strand having nucleic acid sequence of SEQ ID NOS: 1, 3, 5 or 7.

Such antisense oligonucleotides can be used to down regulate expression as further detailed hereinunder. Such an antisense oligonucleotide is readily synthesizable using solid phase oligonucleotide synthesis.

The ability to chemically synthesize oligonucleotides and analogs thereof having a selected predetermined sequence offers means for down-modulating gene expression, as well as for altering or restoring the expression of a given gene. Three types of gene expression modulation strategies may be considered.

At the transcription level, antisense or sense oligonucleotides or analogs that bind to the genomic DNA by strand displacement or the formation of a triple helix may prevent transcription. At the transcript level, antisense oligonucleotides or analogs that bind target mRNA molecules lead to the enzymatic cleavage of the hybrid by intracellular RNaseH. In this case, by hybridizing to the targeted mRNA, the oligonucleotides or oligonucleotide analogs provide a duplex hybrid recognized and destroyed by the RNaseH enzyme. Alternatively, such hybrid formation may lead to interference with correct splicing, which may results in down regulation of the gene expression but may also modulate the expression of novel splice variants.

At the translation level, antisense oligonucleotides or analogs that bind target mRNA molecules prevent, by steric hindrance binding of essential translation factors (ribosomes), to the target mRNA a phenomenon known in the art as hybridization arrest, disabling the translation of such mRNAs.

Thus, antisense sequences, which as described hereinabove may arrest or modify the expression of any endogenous and/or exogenous gene depending on their specific sequence, are subjects for the development of a new pharmacological tool. In addition, radio labeled or otherwise labeled antisense oligonucleotides can be used as diagnostic tools, in vitro as well as in vivo, for example for imaging a specific mRNA, for monitoring antisense chemotherapy, and for protein imaging.

For efficient in vivo application of antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity.

Unmodified oligonucleotides are typically impractical for use as antisense sequences since they have short in vivo half-lives, during which they are degraded rapidly by nucleases. Furthermore, they are difficult to prepare in more than milligram quantities. In addition, such oligonucleotides are poor cell membrane penetraters.

Thus it is apparent that in order to meet all the above listed requirements, oligonucleotide analogs need to be devised in a suitable manner, as described herein below.

Oligonucleotide Analogs

Oligonucleotide analogs are produced in order to improve half-life as well as membrane penetration. Oligonucleotides can be modified either in the base, the sugar or the phosphate moiety. These modifications include, for example, the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester bridges, carbonate bridges, carboxymethyl ester bridges; acetamide bridges, thioether bridges, sulfoxy bridges, sulfono bridges, various "plastic" DNAs, α-anomeric bridges and borane derivatives.

International Patent Application WO 89/12060 discloses various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking or ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—$SO_2$—).

International Patent Application WO 92/20702 describe an acyclic oligonucleotide which includes a peptide backbone on which any selected chemical nucleobases or analogs are stringed and serve a coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other. PNA oligomers can be synthesized from the four protected monomers containing thymine, cytosine, adenine and guanine by Merrifteld solid-phase peptide synthesis. In order to increase solubility in water and to prevent aggregation, a lysine amide group is placed at the C-terminal region.

Thus, in one preferred aspect antisense technology requires pairing of messenger RNA with an oligonucleotide to form a double helix that inhibits translation. The concept of antisense-mediated therapy was already introduced in 1978 for cancer therapy. This approach was based on certain genes that are crucial in cell division and growth of cancer cell. Synthetic fragments of genetic substance DNA can achieve this goal. Such molecules bind to the targeted gene molecules in RNA of tumor cells, thereby inhibiting the translation of the target and resulting in dysfunctional growth of these cells. Other mechanisms have also been proposed. These strategies have been used with some success is treatment of cancers, as well of other illnesses, including viral and other infectious diseases. Antisense oligonucleotides are typically synthesized in lengths of 13-30 nucleotides. The life span of oligonucleotide molecules in blood is rather short. Thus, they have to be chemically modified to prevent destruction by ubiquitous nucleases present in the body. Phosphorothioates are very widely used modification in antisense oligonucleotide ongoing clinical trials. A new generation of antisense molecules consists of hybrid antisense oligonucleotide with a central portion of synthetic DNA while four bases on each end have been modified with 2'O-methyl ribose to resemble RNA. In pre-clinical studies in laboratory animals, such compounds have demonstrated greater stability to metabolism in body tissues and an improved safety profile when compared with the first-generation unmodified phosphorothioate. Dozens of other nucleotide analogs have also been tested in antisense technology.

RNA oligonucleotides may also be used for antisense inhibition as they form a stable RNA-RNA duplex with the target, suggesting efficient inhibition. However, due to their low stability RNA oligonucleotides are typically expressed inside the cells using vectors designed for this purpose. This approach is favored when attempting to target an mRNA that encodes an abundant and long-lived protein.

Recent scientific publications have validated the efficacy of antisense compounds in animal models of hepatitis, cancers, coronary artery restenosis and other diseases. The first antisense drug was recently approved by the FDA. This drug Fomivirsen, developed by Isis, is indicated for local treatment of cytomegalovirus in patients with AIDS who are intolerant of or have a contraindication to other treatments for CMV retinitis or who were insufficiently responsive to previous treatments for CMV retinitis (Pharmacotherapy News Network).

Several antisense compounds are now in clinical trials in the United States. These include locally administered antivirals, systemic cancer therapeutics. Antisense therapeutics has the potential to treat many life-threatening diseases with a number of advantages over traditional drugs. Traditional drugs intervene after a disease-causing protein is formed. Antisense therapeutics, however, block mRNA transcription/translation and intervene before a protein is formed, and since antisense therapeutics target only one specific mRNA, they should be more effective with fewer side effects than current protein-inhibiting therapy.

A second option for disrupting gene expression at the level of transcription uses synthetic oligonucleotides capable of hybridizing with double stranded DNA. A triple helix is formed. Such oligonucleotides may prevent binding of transcription factors to the gene's promoter and therefore inhibit transcription. Alternatively they may prevent duplex unwinding and, therefore, transcription of genes within the triple helical structure.

Thus, according to a further aspect of the present invention there is provided a pharmaceutical composition comprising the antisense oligonucleotide described herein and a pharmaceutically acceptable carries. The pharmaceutically acceptable carrier can be, for example, a liposome loaded with the antisense oligonucleotide. Formulations for topical administration may include, but are not limited to, lotions, ointments, gels, creams, suppositories, drops, liquids, sprays and powders.

Conventional pharmaceutical carriers, aqueous, powder or oily bases, thickeners and the like may be necessary or desirable. Compositions for oral administration include powders or granules, suspensions or solutions in water or non-aqueous media, sachets, capsules or tablets. Thickeners, diluents, flavorings, dispersing aids, emulsifiers or binders may be desirable. Formulations for parenteral administration may include but are not limited to, sterile aqueous solutions which may also contain buffers, diluents and other suitable additives.

According to still a further aspect of the present invention there is provided a ribozyme comprising the antisense oligonucleotide described herein and a ribozyme sequence fused thereto. Such a ribozyme is readily synthesizable using solid phase oligonucleotide synthesis.

Ribozymes are being increasingly used for the sequence-specific inhibition of gene expression by the cleavage of mRNAs encoding proteins of interest. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of Vascular Endothelial Growth Factor receptor (VEGF-r), a key component in the angiogenesis pathway. Ribozyme Pharmaceuticals, Inc., as well as other firms has demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated-WEB home page).

Diagnostic Applications

The present invention also relates to diagnostic assays for the detection of a condition, disease or disorder, optionally and preferably in a sample taken from a subject (patient). The sample taken from the subject can be selected from one or more of blood, serum, plasma, blood cells, urine, sputum, saliva, stool, spinal fluid, lymph fluid, the external sections of the skin, respiratory, intestinal, and genitourinary tracts, tears, milk, neuronal tissue, and any human organ and tissue. The assays are optionally NAT (nucleic acid amplification technology)-based assays as described herein below, such as PCR for example (or variations thereof such as real-time PCR for example). Optionally and preferably the assays may feature detection of a protein and/or peptide, for example by using an antibody for such detection. Non-limiting examples of immunoassays encompassed by the present invention include a Western blot assay or an ELISA, although other immunoassays could optionally be used. The assays may also optionally encompass nucleic acid hybridization assays. The assays may optionally be qualitative or quantitative.

Glycoprotein hormones are known to modulate a number of the cell functions, including modulation of protein activity related to GPH/GPH receptor interaction; modulation of cell proliferation; regulation of cell differentiation and regulation of reproductive function. For example, it has been recently shown that hCG promotes angiogenesis, and therefore has an important function in uterine adaptation to early pregnancy as well as in tumor development (Zygmunt M. et al., 2002, J Clin Endocrinol Metab 87(11):5290-5296), specifically in the development of prostate cancer (Dimhofer S. et al., 1998, Prostate 35(3):212-220). GPH α- and β-chains form four hormones: HCG, LH, FSH and TSH. Each of these hormones participate in different biological pathways, hence, their level in a specific sample may provide a different diagnosis. Specifically, detecting the level of HCG may be used for diagnosing pregnancy (normal and ectopic); trophoblastic tumors (Hydatidiform moles and choriocarcinomas); tumors of the testes (seminomas and nonseminomas); other cancers including breast, colorectal, lung and ovary cancer; and benign conditions including cirrhosis, duodenal ulcer, and inflammatory bowel disease). LH or FSH level can be used to determine fertility and infertility, including determining the timing of ovulation; pituitary diseases; general hormonal imbalance; precocious puberty; and amenorrhea. In samples of male subjects monitoring the LH level is part of the assessment of hypogonadism, and in samples obtained from females FSH level is used to diagnose ovarian cysts. Detecting the level of TSH may be used for diagnosing of thyroid diseases, including hyperthyroidism and hypothyroidism; pituitary diseases (hypopituitarism or hyperpituitarism); under active thyroid in newborns; and female infertility problems. TSH level can also be used to monitor thyroid replacement therapy or antithyroid therapy such as medications, surgery, or radiation.

The hGPH α-chain splice variants described herein are non-limiting examples of markers for diagnosing the above described disease condition(s). Each splice variant marker of the present invention can be used alone or in combination, for various uses, including but not limited to, prognosis, prediction, screening, early diagnosis, determination of progression, therapy selection and treatment monitoring of one of the above-described conditions, diseases or disorders.

Hybridization Assays

Detection of a nucleic acid of interest in a biological sample may optionally be effected by hybridization-based assays using an oligonucleotide probe.

Hybridization based assays which allow the detection of a variant of interest (i.e., DNA or RNA) in a biological sample rely on the use of oligonucleotide which can be 10, 15, 20, or 30 to 100 nucleotides long, preferably from 10 to 50, more preferably from 40 to 50 nucleotides long.

Hybridization of short nucleic acids (below 200 bp in length, e.g. 17-40 bp in length) can be effected using the following exemplary hybridization protocols which can be modified according to the desired stringency; (i) hybridization solution of 6×SSC and 1% SDS or 3 M TMACI, 0.01 M sodium phosphate (pH 6.8), 1 mM EDTA (pH 7.6), 0.5% SDS, 100 mg/ml denatured salmon sperm DNA and 0.1% nonfat dried milk, hybridization temperature of 1-1.5° C. below the $T_m$, and final wash solution of 3 M TMACI, 0.01 M sodium phosphate (pH 6.8), 1 mM EDTA (pH 7.6), 0.5% SDS at 1-1.5 ° C. below the $T_m$; (ii) hybridization solution of 6×SSC and 0.1% SDS or 3 M TMACI, 0.01 M sodium phosphate (pH 6.8), 1 mM EDTA (pH 7.6), 0.5% SDS, 100 mg/ml denatured salmon sperm DNA and 0.1% nonfat dried milk, hybridization temperature of 2-2.5° C. below the $T_m$, and final wash solution of 3 M TMACI, 0.01 M sodium phosphate (pH 6.8), 1 mM EDTA (pH 7.6), 0.5% SDS at 1-1.5° C. below the $T_m$, and final wash solution of 6×SSC, at 22° C.; (iii) hybridization solution of 6×SSC and 1% SDS or 3 M TMACI, 0.01 M sodium phosphate (pH 6.8), 1 mM EDTA (pH 7.6), 0.5% SDS, 100 mg/ml denatured salmon sperm DNA and 0.1% nonfat dried milk, hybridization temperature as appropriate.

The detection of hybrid duplexes can be carried out by a number of methods. Typically, hybridization duplexes are separated from unhybridized nucleic acids and the labels bound to the duplexes are then detected. Such labels refer to radioactive, fluorescent, biological or enzymatic tags or labels of standard use in the art. A label can be conjugated to either the oligonucleotide probes or the nucleic acids derived from the biological sample.

For example, oligonucleotides of the present invention can be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently labeled oligonucleotide probes are used, fluorescein, lissamine, phycoerythrin, rhodamine (Perkin Elmer Cetus), Cy2, Cy3, Cy3.5, Cy5, Cy5.5, Cy7, FluorX (Amersham) and others (e.g., Kricka et al., 1992, Academic Press San Diego, Calif.) can be attached to the oligonucleotides.

Hybridization assays (or assays with a hybridization component) include PCR, RT-PCR, Real-time PCR, RNase protection, in-situ hybridization, primer extension, Southern blots (DNA detection), dot or slot blots (DNA, RNA), and Northern blots (RNA detection) (NAT type assays are described in greater detail below). More recently, PNAs have been described (Nielsen et al., 1999, Current Opin. Biotechnol. 10:71-75). Other detection methods include kits containing probes on a dipstick setup and the like.

Although the present invention is not specifically dependent on the use of a label for the detection of a particular nucleic acid sequence, such a label might be beneficial, by increasing the sensitivity of the detection.

Furthermore, it enables automation. Probes can be labeled according to numerous well-known methods (Sambrook et al., 1989, supra). Non-limiting examples of radioactive labels include $^3$H, $^{14}$C, $^{32}$P, and $^{35}$S. Non-limiting examples of detectable markers include ligands, fluorophores, chemiluminescent agents, enzymes, and antibodies. Other detectable markers for use with probes, which can enable an increase in sensitivity of the method of the invention, include biotin and radio-nucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma ATP and polynucleotide kinase, using the Klenow fragment of Pol I of E coli in the presence of radioactive dNTP (i.e. uniformly labeled DNA probe using random oligonucleotide primers in low-melt gels), using the SP6/T7 system to transcribe a DNA segment in the presence of one or more radioactive NTP, and the like.

Those skilled in the art will appreciate that wash steps may be employed to wash away excess target DNA or probe as well as unbound conjugate. Further, standard heterogeneous assay formats are suitable for detecting the hybrids using the labels present on the oligonucleotide primers and probes.

It will be appreciated that a variety of controls may be usefully employed to improve accuracy of hybridization assays. For instance, samples may be hybridized to an irrelevant probe and treated with RNase A prior to hybridization, to assess false hybridization.

Probes of the invention can be utilized with naturally occurring sugar-phosphate backbones as well as modified backbones including phosphorothioates, dithionates, alkyl phosphonates and a-nucleotides and the like. Modified sugar-phosphate backbones are generally taught by Miller, 1988, Ann. Reports Med. Chem. 23:295 and Moran et al., 1987, Nucleic acid molecule. Acids Res., 14:5019. Probes of the invention can be constructed of either ribonucleic acid (RNA) or deoxyribonucleic acid (DNA), and preferably of DNA.

Optionally and preferably, such probes are constructed according to the nucleotide sequences corresponding to the tail and/or insertion and or bridge portions of the hGPH α-chain splice variants according to the present invention, as described herein above.

NAT Assays

Detection of a nucleic acid of interest in a biological sample may also optionally be effected by NAT-based assays, which involve nucleic acid amplification technology, such as PCR for example (or variations thereof such as real-time PCR for example).

Amplification of a selected, or target, nucleic acid sequence may be carried out by a number of suitable methods. See generally Kwoh et al., 1990, Am. Biotechnol. Lab. 8:14. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the q3 replicase system and NASBA (Kwoh et al., 1989, Proc. Natl. Acad. Sci. USA 86:1173-1177; Lizardi et al., 1988, BioTechnology 6:1197-1202; Malek et al., 1994, Methods Mol. Biol., 28:253-260; and Sambrook et al., 1989, supra).

Polymerase chain reaction (PCR) is carried out in accordance with known techniques, as described for example, in U.S. Pat. Nos. 4,683,195; 47683,202; 4,800,159; and 4,965,188 (the disclosures of which incorporated herein by reference). In general, PCR involves a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following EtBr staining of the DNA following gel electrophores, or using a detectable label in accordance with known techniques, and the like. For a review of PCR techniques, see PCR Protocols, A Guide to Methods and Amplifications, Michael et al. Eds, Acad. Press, 1990.

Optionally and preferably, such primers are constructed according to the nucleotide sequences corresponding to the tail and/or insertion and/or bridge portions of the hGPH α-chain splice variants according to the present invention, as described above.

Ligase chain reaction (LCR) is carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392-396; and ibid., 1992, Nucleic Acids Res. 20:1691-1696).

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification. As commonly known in the art, the oligonucleotides are designed to bind to a complementary sequence under selected conditions.

In one particular embodiment, amplification of a nucleic acid sample from a patient is amplified under conditions which favor the amplification of the most abundant differentially expressed nucleic acid. In one preferred embodiment, RT-PCR is carried out on an mRNA sample from a patient under conditions which favor the amplification of the most abundant mRNA. In another preferred embodiment, the amplification of the differentially expressed nucleic acids is carried out simultaneously. Of course, it will be realized by a person skilled in the art that such methods could be adapted for the detection of differentially expressed proteins instead of differentially expressed nucleic acid sequences.

The nucleic acid (i.e. DNA or RNA) for practicing the present invention may be obtained according to well-known methods.

Oligonucleotide primers of the present invention may be of any suitable length, depending on the particular assay format and the particular needs and targeted genomes employed. In general, the oligonucleotide primers are at least 12 nucleotides in length, preferably between 15 and 24 molecules, and they may be adapted to be especially suited to a chosen nucleic acid amplification system. As commonly known in the art, the oligonucleotide primers can be designed by taking into consideration the melting point of hybridization thereof with its targeted sequence (see in Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

Diagnostic Applications of Antibodies

In another embodiment of the present invention, an immunoassay can be used to qualitatively or quantitatively detect and analyze markers in a sample. This method comprises: providing an antibody that specifically binds to a marker; contacting a sample with the antibody; and detecting the presence of a complex of the antibody bound to the marker in the sample.

Optionally and preferably, such antibodies are prepared according to the amino acid sequences corresponding to the tail and/or insertion and/or bridge portions of the hGPH α-chain splice variants according to the present invention, as described herein above.

The detection and/or quantifying of a marker can be made using any of a number of well-recognized immunological binding assays (see, e.g., U.S. Pat. Nos. 4,366,241; 4,376,110; 4,517,288; and 4,837,168). Useful assays include, for example, an enzyme immune assay (EIA) such as enzyme-linked immunosorbent assay (ELISA), a radioimmune assay (RIA), a Western blot assay, or a slot blot assay. For a review of the general immunoassays, see also, Methods in Cell Biology: Antibodies in Cell Biology, volume 37 (Asai, ed. 1993); Basic and Clinical Immunology (Stites and Terr, eds., 7th ed. 1991).

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a substrate as described above. The sample is preferably a biological fluid sample taken from a subject. Examples of biological fluid samples include blood, serum, urine, prostatic fluid, seminal fluid, semen, seminal plasma and prostate tissue (e.g., epithelial tissue, including extracts thereof) as well as amniotic fluid. In a preferred embodiment, the biological fluid comprises seminal plasma. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads, fluorescent dyes, radiolabels, enzymes (e.g., horse radish peroxide, alkaline phosphatase and others commonly used in an ELISA), and calorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker are incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations and the like. Usually the assays will be carried out at ambient temperature, although they can be conducted over a range of temperatures, such as 10° C. to 40° C.

Pharmaceutical Composition for Regulation of GPH Activity

According to yet another aspect the present invention provides a pharmaceutical composition comprising, as an active ingredient, an hGPH α-chain splice variant for regulating GPH activity in vivo or in vitro. The following embodiments of the present invention are directed at intervention with GPH activity and therefore with GPH receptor signaling.

According to yet another aspect the present invention provides a method of regulating an endogenous protein affecting GPH receptor activity in vivo or in vitro.

According to one embodiment, the method according to this aspect of the present invention comprises the step of administering an agent for regulating the endogenous protein activity in vivo, the endogenous protein having at least one GPH agonist or antagonist activity.

According to one embodiment, the method comprises the step of administering an agent for regulating the endogenous protein activity in vivo, the endogenous protein comprising amino acids sequence at least 80%, preferably at least 90%, more preferably at least 95% or more, homology to an amino acid sequence set forth in any one of SEQ ID NO:2, 4 and 6.

According to one preferred embodiment, the method comprises the step of administering an agent for regulating the endogenous protein activity in vivo, the endogenous protein comprising amino acids sequence at least 80%, preferably at least 90%, more preferably at least 95% or more, homologous to a polypeptide selected from the group consisting of (a) a polypeptide comprising contiguous amino acids of positions 30 to 60 of SEQ ID NO:2; (b) a polypeptide comprising the sequence RTSRSPEAF (positions 93-101 of SEQ ID NO:4); and (c) a polypeptide comprising contiguous amino acids of positions 30 to 72 of SEQ ID NO:6.

An agent which can be used according to the present invention to up regulate the activity of the endogenous protein can include, for example, an expressible sense polynucleotide comprising a nucleotide sequence selected from the group consisting of SEQ ID NOS: 1, 3, 5, or 7.

According to one preferred embodiment, the agent used according to the present invention to up regulate the activity of the endogenous protein include an expressible sense polynucleotide encoding a polypeptide having amino acid sequence set forth in any one of SEQ ID NO:2, 4 and 6.

According to another preferred embodiment, the agent used according to the present invention to upregulate the activity of the endogenous protein include an expressible sense polynucleotide encoding a polypeptide selected from the group consisting of (a) a polypeptide comprising contiguous amino acids having at least 80%, more preferably at least 90%, more preferably 95% or more homology to positions 30 to 60 of SEQ ID NO:2; (b) a polypeptide comprising the sequence RTSRSPEAF (positions 93-101 of SEQ ID NO:4); and (c) a polypeptide comprising contiguous amino acids having at least 80%, more preferably at least 90%, more preferably 95% or more homology to positions 30 to 72 of SEQ ID NO:6.

An agent which can be used according to the present invention to down regulate the activity of the endogenous protein can include, for example, an expressible antisense polynucleotide comprising a nucleic acid sequence complement to a sequence selected from the group consisting of SEQ ID NOS: 1, 3, 5, or 7.

Alternatively, an agent which can be used according to the present invention to down regulate the activity of the endogenous protein can include, for example, an antisense oligonucleotide or ribozyme which includes a polynucleotide or a polynucleotide analog of at least 10 bases, preferably between 10 and 15, more preferably between 15 and 20 bases, most preferably, at least 17-40 bases which is hybridizable in vivo, under physiological conditions, with a portion of a polynucleotide strand encoding a polypeptide having an amino acid sequence set forth in any one of SEQ ID NO:2, 4 or 6.

According to one currently preferred embodiment, the polynucleotide is hybridizable in vivo, under physiological conditions, with a portion of a polynucleotide strand encoding a polypeptide selected from the group consisting of (a) a polypeptide comprising contiguous amino acids having at least 80%, more preferably at least 90%, more preferably 95% or more homology to positions 30 to 60 of SEQ ID NO:2; (b) a polypeptide comprising contiguous amino acids having at least 80%, more preferably at least 90%, more preferably 95% or more homology to a sequence RTSRSPEAF (positions 93-101 of SEQ ID NO:4); and (c) a polypeptide comprising contiguous amino acids having at least 80%, more preferably at least 90%, more preferably 95% or more homology to positions 30 to 72 of SEQ ID NO:6.

Still alternatively, an agent which can be used according to the present invention to downregulate the activity of the endogenous protein can include, for example, a peptide or a peptide analog representing a stretch of at least 6-10, 10-15, or 15-20 consecutive amino acids or analogs thereof derived from a polypeptide having an amino acid sequence set forth in any one of SEQ ID NO:2, 4 and 6.

According to one currently preferred embodiment the peptide or peptide analog downregulating the activity of the endogenous protein is derived from a polypeptide selected from the group consisting of (a) a polypeptide comprising contiguous amino acids having at least 80%, more preferably at least 90%, more preferably 95% or more homology to positions 30 to 60 of SEQ ID NO:2; (b) a polypeptide comprising contiguous amino acids having at least 80%, more preferably at least 90%, more preferably 95% or more homology to a sequence RTSRSPEAF (positions 93-101 of SEQ ID NO:4); and (c) a polypeptide comprising contiguous amino acids having at least 80%, more preferably at least 90%, more preferably 95% or more homology to positions 30 to 72 of SEQ ID NO:6.

Peptides or peptide analogs containing the interacting GPH α-chain domain according to the present invention will compete by protein interactions to form protein complexes with GPH receptor, inhibiting or accelerating the pathways in which GPH α-chain is involved. Such peptides or peptide analogs may optionally comprise and/or be derived from the tail, bridge and/or insertion portions of the hGPH α-chain splice variants of the present invention as described herein above.

The following biochemical and molecular systems are known for the characterization and identification of protein-protein interaction as well as of peptides as substrates, through peptide analysis, which systems can be used to identify inhibitory peptide sequences. One such system employs introduction of a genetic material encoding a functional protein or a mutated form of the protein, including amino acid deletions and substitutions, into cells. This system can be used to identify functional domains of the protein by the analysis of its activity and the activity of its derived mutants in the cells. Another such system employs the introduction of small encoding fragments of a gene into cells, e.g., by means of a display library or a directional randomly primed cDNA library comprising fragments of the gene, and analyzing the activity of the endogenous protein in their presence (see, for example, Gudkov et al., 1993, Proc. Natl. Acad. Sci. USA 90:3231-3236; Gudkov and Robinson, 1997, Methods Mol Biol 69:221-240; and Pestov et al., 1999, Bio Techniques 26:102-106). Yet an additional system is realized by screening expression libraries with peptide domains, as exemplified, for example, by Yamabhai et al. (1998, J Biol Chem 273: 31401-31407). In yet another such system overlapping synthetic peptides derived from specific gene products are used to study and affect in vivo and in vitro protein-protein interactions. For example, synthetic overlapping peptides derived from the HIV-1 gene (20-30 amino acids) were assayed for different viral activities (Baraz et al., 1998, FEBS Letters 441:419-426) and were found to inhibit purified viral protease activity; bind to the viral protease; inhibit the Gag-Pol polyprotein cleavage; and inhibit mature virus production in human cells.

Other agents according to the present invention may optionally include an antibody capable of specifically recognizing an epitope of hGPH α-chain splice variant of the present invention, wherein such an epitope preferably comprises a tail and/or insertion portion as described herein above. Such an antibody may have a therapeutic utility in blocking or decreasing the activity of the hGPH α-chain splice variant protein in pathological conditions where beneficial effect can be achieved by such a decrease. The antibody employed is preferably a humanized monoclonal antibody, produced by known globulin-gene library methods. The antibody is administered typically as a sterile solution by IV injection, although other parenteral routes may be suitable. Typically, the antibody is administered in an amount between about 1-15 mg/kg body weight of the subject. Treatment is continued, e.g., with dosing every 1-7 days, until a therapeutic improvement is seen.

According to yet another aspect the present invention relates to hGPH α-chain splice variants capable of targeting a therapeutic or a diagnostic agent to a cell bearing GPH receptors.

According to one embodiment, the present invention provides a conjugate of the hGPH α-chain splice variant of the present invention with a therapeutic or a diagnostic agent. In general, the drugs conjugated to the hGPH α-chain splice variants of the present invention will be those desired to act in the proximity of the receptors to which the hormones ordinarily bind. Suitable provision for release of the drug from the conjugate will be also included in the conjugate.

According to another embodiment, the present invention provides a method for targeting a therapeutic or diagnostic agents to a cell bearing a GPH receptor, comprising administering to a subject in need thereof a pharmaceutical composition comprising as an active ingredient a hGPH-α-chain splice variant of the present invention conjugated to the therapeutic or diagnostic agent.

According to one embodiment, the therapeutic or the diagnostic agent is selected from the group consisting of a cytotoxic compound, a cytostatic compound, an antisense compound, an anti-viral agent, a specific antibody, a biodegradable carrier an imaging agent and a detection agent.

Suitable therapeutic agents that may be conjugated include peptides or proteins such as insulin-like growth factors; epidermal growth factors; acidic and basic fibroblast growth factors; platelet-derived growth factors; various colony stimulating factors, such as granulocyte CSF, macrophage-CSF, and the like; as well as various cytokines such as IL-2, IL-3 and the plethora of additional interleukin proteins; various interferons; tumor necrosis factor; and the like. Also, small molecule drugs such as antibiotics, anti-inflammatories, toxins, and the like can be used.

According to another embodiment, the diagnostic agent is an imaging compound selected from, but not restricted to paramagnetic particles: gadolinium, yttrium, lutetium and gallium; radioactive moieties: radioactive indium, rhenium and technetium; fluorescent dyes: fluorescein isothiocyanate (FITC), green fluorescent protein, rhodamine I, II, III and IV, rhodamine B and rosamine.

The principles of the invention, disclosing novel hGPH α-chain splice variants, polynucleotides encoding same, methods of productions, pharmaceutical composition comprising same and methods for use may be better understood with reference to the following non-limiting examples.

EXAMPLES

Example 1

Identification of hGPH α-Chain Splice Variants

The mRNAs sequences of the known hGPH α-chain (NM_000735; SEQ ID NO:9) was used for screening an EST database for novel splice variants using proprietary algorithm for clustering and assembly of nucleic acid sequences (the method for mRNA clustering and assembly used described in U.S. patent application Ser. No. 09/133,987. The screening and annotation method described in U.S. patent application Ser. No. 10/426,002, 10/242,799 assigned to the assignee of the present invention). Two splice variants were found based on ESTs: the first was based on EST 602592885F1, GenBank accession number BG571584 (SEQ ID NO:10), using human placenta NIH_MGC_79 library.

The obtained splice variant 1, having a nucleic acid sequence of SEQ ID NO:1, is the results of the insertion of a novel in-frame exon (exon 2A), based on ALU sequence within the intron (FIG. 2A). This splice variant encodes for a polypeptide, having SEQ ID NO:2, comprising 147 amino acids (FIG. 2B).

The second splice variant was based on the following ESTs: EST AV746586, GenBank accession number AV746586 (SEQ ID NO:11), using human pituitary NPC library; EST C17299, GenBank accession number C17299 (SEQ ID NO:12), using Clontech human aorta polyA+ mRNA (#6572) library; EST 602508788F1, GenBank accession number BG436344 (SEQ ID NO:13), using human placenta NIH_MGC_79 library; and EST 602508669F1, GenBank accession number BG436248 (SEQ ID NO:14), using human placenta NIH_MGC_79 library.

As shown in FIG. 3A, this splice variant (variant 2) results from the retention of intron 3 between exons 3 and 4 (SEQ ID NO:3), encoding for a 101 amino acid polypeptide (SEQ ID NO:4, FIG. 3B).

These two EST-based novel splice variants comprise polynucleotides encoding polypeptides that retain the glycoprotein hormone domain.

Additional two splice variants were identified utilizing primers designed for the amplification of the above described splice variants (SEQ ID NOs: 1 and 3).

The primers used were as follows:

Primer ACNF Forward: Positions 79-101 of the native hGPH α-chain (SEQ ID NO:8)-5' aaagcccagagaaaggagcgcc 3' (SEQ ID NO: 16).

Primer ACNR Reverse: Positions 375-400 of the native hGPH α-chain (SEQ ID NO:8)-5' actttgaaacccccccattactgtgacc 3' (SEQ ID NO:17).

Primer ACV1F Forward: exon 2A, positions 191-213 of SEQ ID NO:1 5'gacagggtttcaccatgttgccc 3' (SEQ ID NO: 18).

Primer ACV1R Reverse: exon 2A, positions 252-281 of SEQ ID NO:1-5' ccttagtgggtggattgcttgag 3' (SEQ ID NO:19).

Primer ACV2R Reverse: intron 3, positions 549-574 of SEQ ID NO:3-5' attctgaataaatccagtctataccc 3' (SEQ ID NO:20).

The additional PCR-derived splice variants encode a polypeptide in which the glycoprotein hormone domain is replaced with a unique amino acid sequence having homology to the eukaryotic protein of unknown function (Pfam database, DUF846, SEQ ID NO:15). One such splice variant (variant 3) comprises 879 nucleotides (SEQ ID NO:5, FIG. 4) encoding a polypeptide of 72 amino acids (SEQ ID NO:6). Variant 4 comprises 1295 nucleic acids (SEQ ID NO:7, FIG. 5) encoding the same polypeptide of 72 amino acids (SEQ ID NO:6, FIG. 6). Both PCR-derived splice variants were found in Placenta (pool), and in Cervix (pool including HeLa cell line). Small amounts of variant 4 (SEQ ID NO:7, nucleic acid sequence) were also found in brain tissue.

FIG. 7 shows the nucleic acid sequence of WT (previously known) GPH α-chain (SEQ ID NO:8) and its deduced amino acids sequence (SEQ ID NO:9).

Example 2

Expression of hGPH α-Chain Splice Variants 2 and 3

The expression of the splice variants identified by ESTs was examined by RT-PCR. Variant 1, having the nucleic acid sequence set forth in SEQ ID NO: 1, was found almost exclusively in Placenta (pool), and very weakly in Testis (pool). The primers used for the RT-PCR reaction were primer "ACNR" and "ACV1F" described herein above, having the nucleic acid sequence set forth in SEQ ID NO:17 and NO:18, respectively.

Variant 2 having the nucleic acid sequence set forth in SEQ ID NO:3 was detected by RT-PCR in cDNA samples taken from Human Cervix, Uterus, Ovary, Placenta, Breast, Prostate and Testis. The primers used were the primers having the nucleic acid sequence set forth in SEQ ID NOS: 16 and 17, as described herein above. This splice variant was also detected, utilizing the primers ACNF (SEQ ID NO:16) and ACV1R (SEQ ID NO:19) in cDNA samples taken from human cervix and placenta. Weak expression was also obtained in sample taken from uterus.

Example 3

Functional Assay of hGPH α-Chain Splice Variant 1 of the Invention

The activity of an FSH glycoprotein hormone composed of a WT β-chain and α-chain splice variant 1 having the nucleic acid sequence set forth in SEQ ID NO:1 was examined by Protalix Ltd., Carmiel, Israel.
Obtaining FSH-producing Cell Lines
Production of Expression Cassettes
Alpha chain variant 1 (nucleic acid sequence of SEQ ID NO:1) and wild type ORFs were inserted into a plant expression vector called "CE" received from Protalix (Carmiel, Israel). The vector includes a selection marker which grants resistance to Ampicilin. In addition the vector contains OCSter and 35S+ Omega needed for gene expression in plants.
The variant inserts were generated using PCR by using primers planned to cover the ATG of the ORF and the TAG/TAA of either variants and WT (known alpha chain protein, SEQ ID NOs: 8 and 9).
The forward primer was the same for WT and the variant (ForW12, SEQ ID NO:21, see below), and included a repeat of AAAA upstream to the ATG and a restriction site for EcoR1 restriction enzyme (underlined).
The reverse primers were also the same for WT and variant #1 (RevW1, SEQ ID NO:22, see below) included a restriction site for the restriction enzyme Sal1 (underlined).
Primer Sequences:

```
ForW12:                              (SEQ ID NO:21)
5'acgcgtcgacaaaaatggattactacagaaaaatatgcagc-3'

RevW1:                               (SEQ ID NO:22)
5'-cggaattcctattaagatttgtgataataacaagtactgc-3'
```

PCR was performed by increasing the annealing temperature from 51° C. to 62° C. after 9 cycles.

PCR was done on cDNA derived by RT, from total RNA of four tissue samples:
1) A pool of cervix
2) HeLa cell-line
3) A pool of placenta
4) A pool of testis
Reaction was performed according to the Hot Start protocol of HotStar™ (Qiagen).
Reaction plan was as follows:
95° C.-5 minutes (polymerase activation)
94° C.-45 seconds (denaturation)
51° C.-45 seconds (annealing)
72° C.-60 seconds (polymerization)>>for 9 cycles
94° C.-45 seconds (denaturation)
52° C.-45 seconds (annealing)
72° C.-60 seconds (polymerization)>>for 26 cycles
72° C.-10 minutes
PCR products were run on a 2% agarose gel. Variant 1 was not produced by the ForW12 and RevW1 primers alone, and was stitched by mixing two fragments created by same PCR conditions only with a set of two internal primers:
One fragment was established by using ForW12 and an internal Reverse primer; second fragment was established by using an overlapping internal Forward primer and RevW1. It should be noted that this probably reflects a less common variant which is also longer, and which therefore will not be amplified as efficiently by PCR.
The two fragments were mixed and annealed and underwent another PCR reaction with the same conditions using both primers ForW12 and RevW1 to create the Var#1 insert fragment.
The bands of the previously known as well as variant #1 were extracted from the gel and sent for direct sequencing. When sequence was validated for all PCR fragments, all products, as well as the CE vector, were digested by both EcoR1 and Sal1 restriction enzymes, to create sticky ends for cloning.
The CE vector was also digested by EcoR1 alone for control.
All digestions were tested on a 2% Agarose gel and were found to be of the right sizes.
Cloning of all variant inserts into the CE vector was done by a ONE STEP LIGATION KIT. Ligation confirmation was done by direct sequencing of the insert using vector specific primers. Final insert containing vectors were transfected into competent E. Coli bacteria by a standard transfection protocol. Bacteria were spread on Ampicilin-containing selection plates, and colonies grown were isolated and presence of the cloned vector was confirmed by direct sequencing of the colony DNA. Isolated, confirmed colonies were proliferated in selection medium, and were frozen in −70° C.
The vector used for introducing the β chain gene was an already built construct named pGreenII-nos-Kana-LR (provided by Protalix Ltd, Carmiel, Israel), carrying all of the components of the CE plant expression cassette (obtained from Prof Galili from the Weizmann Institute, also disclosed in U.S. Pat. No. 5,367,110) with a non-relevant gene (L) targeted to the chloroplast and cloned in the EcII36II restriction site. In the cloning steps that were performed, the non-relevant gene with its N-Terminal signal was excised out with SalI and PstI (Roche, 348783 and 621625 respectively), and was further used to subclone a SalI-PstI insert harboring the P chain gene.
Construction of Expression Plasmid
The polynucleotides encoding GPH α-chain (known protein; SEQ ID NOs: 8 and 9) and splice variant 1 were introduced into the binary vector pGreen II obtained from Dr. P. Mullineaux (Hellens P. et al., 2000, Plant Mol Biol 42:819-832).
Cloning Process for wt GPHα-chain:
All of the following steps for cloning were performed in accordance with conditions provided by the manufacturers.
The α-chain gene (WT α) cloned in the CE expression cassette was incubated for 2 hours with SmaI (Roche, 220566) and Ecl 136II (Fermentas, #EROO25). The pGreen II nos-kana FSHβ-NS cassette was cut with SmaI. The vector was first dephosphorylated (Shrimp Alkaline Phosphatase of Roche, 1758250) and than ligated with the above inserts (T4 DNA Ligase of Invitrogen, 15224-025), forming the final expression vector
Cloning process for GPH α-chain splice variant 1 (Var 1; α1 has Ecl136II restriction site in the coding region hindering the use of this enzyme for subcloning):
The α1 chain expression cassette was cut with SmaI and NotI (Roche, 1014706). The sticky end was filled in using Klenow Enzyme (Roche, 1008404). The fragments were run out on a 1% Agarose gel (Sigma, A-6013) using a 1×TAE running buffer (Biorad, #161-0773) and the desired fragment was then eluted from the gel (GIBCOBRL, Concert™ Rapid Gel Extraction System, 11456-027) for the subsequent ligation described below. Next, the pGreen II nos-kana FSHβ cassette was cut with SmaI. The vector was dephosphorylated and ligated with the corresponding insert, forming the final expression vector.

Kanamycin resistance is conferred by the NPTII gene driven by the nos promoter obtained together with the pGreen II vector.

The resulting plasmid was sequenced to ensure correct cloning using the following sequencing primers (Sigma): 5' 35S promoter: 5'-ctcagaagaccagagggc-3' (SEQ ID NO:23), and the 3' terminator: 5'-caaagcggccatcgtgc-3' (SEQ ID NO:24).

The vector further included a polynucleotide encoding a WT (previously known) GPH β-chain, subcloned in the same orientation, a native signal to target the expression products to the apoplast and NPTII gene as a selection marker. Expression from pGreen II vector is controlled by the 35S promoter from Cauliflower Mosaic Virus, the TMV (Tobacco Mosaic Virus) omega translation enhancer element and the octopine synthase terminator sequence from *Agrobacierium tumefaciens*.

Transformation of Carrot Cells and Isolation of Transformed Cells

Establishment of carrot callus and cell suspension cultures was performed as described previously by Torres K. C. (Tissue culture techniques for horticultural crops, p.p. 111, 169).

Transformation of carrot cells was preformed using *Agrobacterium* by an adaptation of a method described previously (Wurtele, E. S, and Bulka, K., 1989, Plant Sci. 61:253-262). Cells growing in liquid media were used throughout the process instead of calli. Incubation and growth times were adapted for transformation of cells in liquid culture. Briefly, *Agrobacteria* were transformed with the pGreen II vector by electroporation (den Dulk-Ra, A. and Hooykaas, P. J., 1995, Methods Mol. Biol. 55:63-72). Transformed *Agrobacteria* were selected using 30 mg/ml paromomycine antibiotic. Carrot cells were transformed with *Agrobacterium* and selected using 60 mg/ml of paromomycin antibiotics in liquid media.

Screening of Transformed Carrot Cells for Isolation of Calli Expressing High Levels of Alpha Chain (Native or Variant)

14 days following transformation, cells from culture were plated on solid media at dilution of 3% packed cell volume for the formation of calli from individual clusters of cells. When individual calli reached 1-2 cm in diameter, the cells were homogenized and the total soluble proteins were subjected to detection of the recombinant FSH molecule by an Enzyme-Linked Immunosorbent Assay (DSL, DSL-10-4700) with the protocol supplied by the manufacturer. Calli expressing significant levels of alpha chain (native or variant) were expanded and transferred to a scale-up growth in liquid media. The liquid culture was used for protein extraction and analysis.

Scale Up of Culture Growth in a Bioreactor

A callus of about 1 cm (in diameter) of genetically modified carrot cells containing the appropriate gene was plated onto MS 9-cm diameter agar medium plate containing 4.4 gr/l MSD medium (Duchefa), 9.9 mg/l thiamin HCl (Duchefa), 0.5 mg folic acid (Sigma) 0.5 mg/l biotin (Duchefa), 0.8 g/l Casein hydrolisate (Duchefa), 30 g/l sugar and the hormone 2-4 D (Sigma). The callus was grown for 14 days at 25° C.

Suspension cell culture was prepared by sub-culturing the transformed callus in an MSD liquid medium (Murashige & Skoog (1962) containing 0.2 mg/l 2,4-dichloroacetic acid), as is well known in the art. The suspension cells were cultivated in 250-ml Erlenmeyer flask (working volume started with 25 ml and after 7 days increased to 50 ml) at 25° C. with shaking speed of 60 rpm. Subsequently, cell culture volume was increased to 1 L Erlenmeyer flask by addition of working volume up to 300 ml under the same conditions. Inoculum for a small bioreactor (10 L; for further details see WO98/13469) containing 4 L MSD medium, was obtained by addition of 400 ml suspension cells derived from two 1 L Erlenmeyer flasks that were cultivated for seven days. After a week of cultivation at 25° C. with 1 Lpm airflow, MDS medium was added up to 10 L and the cultivation continued under the same conditions.

FSH Activity Assay

Cells grown in culture were sieved through a 100 mesh sieve, and extracted in an extraction buffer having the following components: 20 Mm buffer phosphate at pH 2, mM EDTA, 20 Mm 1-Ascorbic acid and 0.1 Mm PMSF. An IKA Ultra Turrax T-25 homogenizer equipped with a S-25 N-10 rotor was used for cell homogenization (15 minutes, 24000 rpm at 4° C.). Following a spin of 13000 rpm at 4° C. for 20 min. (Sorval, ss34 rotor) at 4° C., the supernatant was tested with the previously described ELISA. The resulted pellet was then taken for a second round of homogenization, and centrifugation under identical conditions to those described above. The resultant supernatant was added to the one obtained from the first extraction stage.

FSH Activity

FSH activity was studied in immortalized mammalian granulose cells produced by Prof. Abraham Amsterdam from the Weizmann Institute Rehovot, Israel, (Suh B. S. et al., 1992, JBC 119, 439-450; Keren-Tal, D. et al., 1993, Mol. Cell. Endocrinol. 95, R1-R10; Amsterdam A., and Sasson R., 2004, In: The Ovary, Chapter 22, Elsevier press). These cells retain their ability to undergo differentiation and luteinization following treatments elevating intracellular levels of cAMP (paracrine and endocrine factors such as bFGF, glococorticoids, leptin, TNF-α and various non-physiological substances such as phorbol ester and TPA). Increased levels of intracellular cAMP were found to bring about attenuated proliferation rate and high production of pregnenolone, progesterone and 20α dihydroprogesterone.

These immortalized steroidogenic granulose cells, which express 20 times more LH/hCG or FSH receptors than primary cells, can be also used as a reliable tool for biological assay and radio receptor assay for these gonadotropins. In this respect, it was found that stimulation of cells expressing LH/hCG receptor or FSH receptor with increasing doses of gonadotropins result in a dose-dependent increase of cAMP and progesterone. The dose-response data serves as a calibration curve for measuring the gonadotropin bioactivity in biological specimens, such as human sera or pituitary extracts in normal and pathological situation. In this assay, when cells are cultured in the absence of stimulants elevating intracellular cAMP, they proliferate rapidly, showing low expression of the steroidogenic enzymes and releasing small quantities of progesterone. However, on stimulation with gonadotropic hormones, the cells produce high levels of progesterone. This unique feature of immortalized granulose cells enables a detailed analysis of the induction kinetics of the steroidogenic enzymes in a homogeneous cell system.

Determining Fsh Content in the Transformed Cells

Quantitative measurements of FSH in protein extracts isolated from the stably transformed cell lines described above was performed using FSH Enzyme-Linked Immunosorbent Assay (ELISA) Kit (Diagnostic Systems Laboratories, Inc., Webster, Tex. Kit No. DSL-10-4700), according to the manufacturer instructions.

Briefly, The DSL-10-4700 ACTIVE® FSH ELISA is an enzymatically amplified "two-step" sandwich-type immunoassay. In the assay, Standards, Controls and unknown samples are incubated in microtitration wells which have been coated with anti-FSH antibody. After incubation and washing, the wells are treated with another anti-FSH detection antibody labeled with the enzyme horseradish peroxidase (HRP). After a second incubation and washing step, the wells are incubated with the substrate tetramethylbenzidine (TMB). An acidic stopping solution is then added and the degree of enzymatic turnover of the substrate is determined by dual wavelength absorbance measurement at 450 and 620 nm.

The absorbance measured is directly proportional to the concentration of FSH present. A set of FSH Standards is used to plot a standard curve of absorbance versus FSH concentration from which the FSH concentrations in the unknowns can be calculated.

Cell-Based Assay of FSH Activity

FSH activity was assayed in total protein extracts obtained from the transformed cells obtained as describe herein above, diluted in the range of 1:50-1:500. Extract from the following cell lines were examined:

1. Cell line expressing WT α-chain and a WT β-chain.
2. Cell line expressing α-chain splice variant 1 and a WT β-chain Two commercial FSH protein preparations (Serono recombinant human FSH and Ferring purified human FSH) served as a positive control. The activity of the control FSH was studied either at optimal conditions for the FSH protein, and in the presence of 25 μl protein extract from a non-transformed plant cell line. Protein extract from non-transformed plant cell lines served as a negative control.

Immortalized steroidogenic granulose cells were incubated with protein extracts of hFSH-expressing cell lines ("unknown samples"), the control FSH or the extract from non-transformed cells for 24 hours at 37° C. The level of secreted progesterone was subsequently evaluated by a radioimmunoassay (RIA) in the medium using a beta-counter. Calibration curve was prepared using serial dilutions from 0 to 5000 pg progesterone.

FIG. 8 summarizes the specific FSH activity obtained from protein extract of a plant transformed with WT α- and β chains (column 1); protein extract of a plant transformed with α-chain splice variant I and WT β-chain (column 2); Standard FSH (Serono, column 3 and Ferring, column 4), incubated with protein extract of non-transformed cells; and protein extract of non-transformed cells alone (column 5).

The Figure clearly demonstrates that FSH composed of an α-chain splice variant 1 (having the nucleic acid sequence set forth in SEQ ID NO:1) shows an equivalent activity to FSH composed of WT α-chain, as well as to the activity of the standard commercial FSH proteins. It should be noted that the activity of the standard FSH determined in the presence of a protein extract of non-transformed cells was lower compared to its activity without the extract, suggesting that the plant extract comprises unknown substances having inhibitory effects on FSH activity.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

What is claimed is:

1. An isolated polynucleotide comprising the nucleic acid sequence of SEQ ID NO: 1.

2. An isolated polynucleotide encoding a polypeptide having at least one hGPH activity wherein said polynucleotide comprises nucleotides 190-282 of SEQ ID NO: 1 in a polynucleotide of at least 695 bases.

3. The polynucleotide according to claim 1 encoding a polypeptide having at least one hGPH α-chain activity.

4. An isolated polynucleotide comprising a nucleic acid sequence encoding a polypeptide having the sequence set forth in SEQ ID NO: 2.

5. An isolated polynucleotide comprising a nucleic acid sequence complementary to the nucleic acid sequence according to claim 4 or claim 2.

6. An expression vector comprising the polynucleotide sequence of claim 1 or claim 2.

7. A host cell comprising the vector according to claim 6.

8. A process for producing a polypeptide which comprises:
   culturing the host cell according to claim 7, wherein the host cell is a transformed carrot cell, under conditions suitable to produce the polypeptide encoded by the polynucleotide; and
   recovering said polypeptide.

9. The process of claim 8, wherein the transformed carrot cell is a cell from carrot callus.

10. The process of claim 8, wherein the conditions comprise culturing the transformed carrot cell in suspension.

* * * * *